(12) United States Patent
Godefroy et al.

(10) Patent No.: US 9,539,315 B2
(45) Date of Patent: Jan. 10, 2017

(54) METHODS, AGENTS AND PEPTIDES FOR INHIBITING MATRIX METALLOPROTEINASE-2 SIGNALING

(75) Inventors: Emmanuelle Godefroy, New York, NY (US); Nina Bhardwaj, West Orange, NJ (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/343,123

(22) PCT Filed: Sep. 10, 2012

(86) PCT No.: PCT/US2012/054380
§ 371 (c)(1),
(2), (4) Date: Jun. 13, 2014

(87) PCT Pub. No.: WO2013/036904
PCT Pub. Date: Mar. 14, 2013

(65) Prior Publication Data
US 2014/0314799 A1    Oct. 23, 2014

Related U.S. Application Data

(60) Provisional application No. 61/573,542, filed on Sep. 8, 2011.

(51) Int. Cl.
| | | |
|---|---|---|
| *G01N 33/00* | (2006.01) | |
| *G01N 33/53* | (2006.01) | |
| *A61K 39/00* | (2006.01) | |
| *C07K 16/28* | (2006.01) | |
| *G01N 33/566* | (2006.01) | |
| *C12N 9/64* | (2006.01) | |
| *C12Q 1/37* | (2006.01) | |
| *G01N 33/573* | (2006.01) | |

(52) U.S. Cl.
CPC ....... *A61K 39/0011* (2013.01); *C07K 16/2896* (2013.01); *C12N 9/6491* (2013.01); *C12Q 1/37* (2013.01); *G01N 33/566* (2013.01); *G01N 33/573* (2013.01); *A61K 39/00* (2013.01); *C07K 2317/76* (2013.01); *G01N 2333/52* (2013.01); *G01N 2333/96494* (2013.01)

(58) Field of Classification Search
None
See application file for complete search history.

(56) References Cited

U.S. PATENT DOCUMENTS

| | | | |
|---|---|---|---|
| 8,481,477 B2 | 7/2013 | Godefroy et al. | |
| 2002/0031817 A1* | 3/2002 | Falduto et al. | 435/226 |
| 2009/0011418 A1 | 1/2009 | Hoon et al. | |
| 2009/0041836 A1* | 2/2009 | Boons | A61K 39/0011 424/450 |
| 2013/0216553 A1* | 8/2013 | Clark | C07K 16/12 424/164.1 |
| 2014/0030216 A1 | 1/2014 | Godefroy et al. | |

FOREIGN PATENT DOCUMENTS

WO    2007/111938    10/2007

OTHER PUBLICATIONS

Sacre et al. The Toll-Like Receptor Adaptor Proteins MyD88 and Mal/TIRAP Contribute to the Inflammatory and Destructive Processes in a Human Model of Rheumatoid Arthritis. The American Journal of Pathology, vol. 170, No. 2, pp. 518-525 (Feb. 2007).*
Abdulkhalek et al, "Neu1 sialidase and matrix metalloproteinase-9 cross-talk is essential for Toll-like receptor activation and cellular signaling", Journal of Biol Chem, 2011, 286:36532-36549.
Arima et al, "Distinct Signal Codes Generate Dendritic Cell Functional Plasticity", 2012, Sci Signal, 3:1-15.
Dreno et al, "Randomized trial of adoptive transfer of melanoma tumor-infiltrating lymphocytes as adjuvant therapy for stage III melanoma", Cancer Immunol Immunother, 2002, 51:539-546.
Egeblad et al., "New functions for the matrix metalloproteinases in cancer progression", Nat Rev Cancr, 2002, 2 (3):161-174.
Gebbia et al., "Selective induction of matrix metalloproteinases by Borrelia burgdorferi via toll-like receptor 2 in monocytes", Journal of Infect Disease, 2004,189:113-119.
Genbank Accession No. AAX43100.1: matrix metalloproteinase 2, partial [synthetic construct] Mar. 21, 2005.
Godefroy et at, "Matrix metalloproteinase-2 conditions human dendritic cells to prime inflammatory TH2 cells via an IL-12- and OX40L-dependent pathway", Cancer Cell, 2011, 19:333-346.
Hofmann et al, "Matrix metalloproteinases in human melanoma", J Invest Dermatol, 2000, 115:337-344.
Khammari, et al., "Longterm follow-up of patients treated by adoptive transfer of melanoma tumor-infiltrating lymphocytes as adjuvant therapy for stage III melanoma", Cancer Immunol Immunother, 2007, 56:1853-1860.
Labarriere et al., "Therapeutic efficacy of melanoma-reactive TIL injected in stage III melanoma patients", Cancer Immunol Immunother, 2002, 51:532-538.

(Continued)

*Primary Examiner* — Elizabeth C Kemmerer
*Assistant Examiner* — Regina M Deberry
(74) *Attorney, Agent, or Firm* — Klauber & Jackson LLC

(57)    ABSTRACT

Screening assays and methods of using same for screening to identify modulator agents or compounds that affect matrix metalloproteinase-2 (MMP-2) mediated activation of toll-like receptor-2 (TLR-2) are described herein. Pharmaceutical and immunogenic compositions comprising agents or compounds that modulate MMP-2 mediated activation of TLR-2 are also encompassed. Methods for modulating MMP-2 mediated activation of TLR-2 using MMP-2 peptides in pharmaceutical and immunogenic compositions, as well as vaccines, are also envisioned. Melanoma is an exemplary tumor type that expresses MMP-2 and for which such pharmaceutical and immunogenic compositions, as well as vaccines, would confer benefit to patients. Also encompassed are methods for reducing MMP-2 mediated activation of TLR-2 and downstream signaling therefrom so as to achieve more effective T cell responses to MMP-2 expressing tumors.

17 Claims, 9 Drawing Sheets

(56) References Cited

OTHER PUBLICATIONS

McCarter et al, "Melanoma skews dendritic cells to facilitate a T helper 2 profile", Surgery, 2005, 138:321-328.
Monaco et al. "Toll-like receptor-2 mediates inflammation and matrix degradation in human atherosclerosis", Circulation, 2009, 120:2462-2469.
Moser et al., "Dendritic cell regulation of TH1-TH2 development", Nat Immunol, 2000, 1:199-205.
So et al., "Signals from OX40 regulate nuclear factor of activated T cells c1 and T cell helper 2 lineage commitment", Proc Natl Acad Sci USA, 2006, 103:3740-3745.
Tatsumi et al., "Disease-associated bias in T helper type 1 (Th1)/Th2 CD4(+) T cell responses against MAGE-6 in HLA-DRB1*0401+ patients with renal cell carcinoma or melanoma", J Exp Med, 2002,196:619-628.
Zhang et al., "TLR1/TLR2 Agonist Induces Tumor Regression by Reciprocal Modulation of Effector and Regulatory T Cells", 2011, The Journal of Immunology, 2011, 186: 1963-1969.
Lauerova et al., "Malignant melanoma associates with Th1/Th2 imbalance that coincides with disease progression and immunotherapy response", Neoplasma, 2002, 49:159-166.
Minkis et al., "TH2-type bias of T cells expanded from the blood of melanoma patients switched to type 1 by IL-12p70 mRNA-transfected dendritic cells", Cancer Res, 2008, 68:9441-9450.
Conroy et al., "TLR ligand suppression or enhancement of Treg cells? A double-edged sword in immunity to tumours", Oncogene, 2008, 27:168-180.
Hoffman et al., "TLR-targeted therapeutics", Nature Rev, 2005, 4:879-880.
Paulos et al., "Toll-like Receptors in Tumor Immunotherapy", Cin Canc Res, 2007, 13:5280-5289.
Amos et al., "Adoptive immunotherapy combined with intratumoral TLR agonist delivery eradicates established melanoma in mice", Canc Immunol Immunotherapy, 2011, 60:671-683.
Goto et al., "Activation of toll-like receptors 2, 3, and 4 on human melanoma cells induces inflammatory factors", Mol Canc Ther, 2008, 7:3642-3653.
Clark et al., "Serine Lipids of Porphyromonas gingivalis are Human and Mouse Toll-Like Receptor 2 Ligands", Infector and Immunity, 2013, 81:3479-3489.
Godefroy et al., "Activation of Toll-like Receptor-2 by Endogenous Matrix Metalloproteinase-2 Modulates Dendritic-Cell-Mediated Inflammatory Responses", Cell Reports, 2014, 9:1856-1870.
Kessenbrock et al., "Matrix Metalloproteinases: Regulators of the Tumor Microenvironment", Cell, 2010, 141:52-67.

* cited by examiner

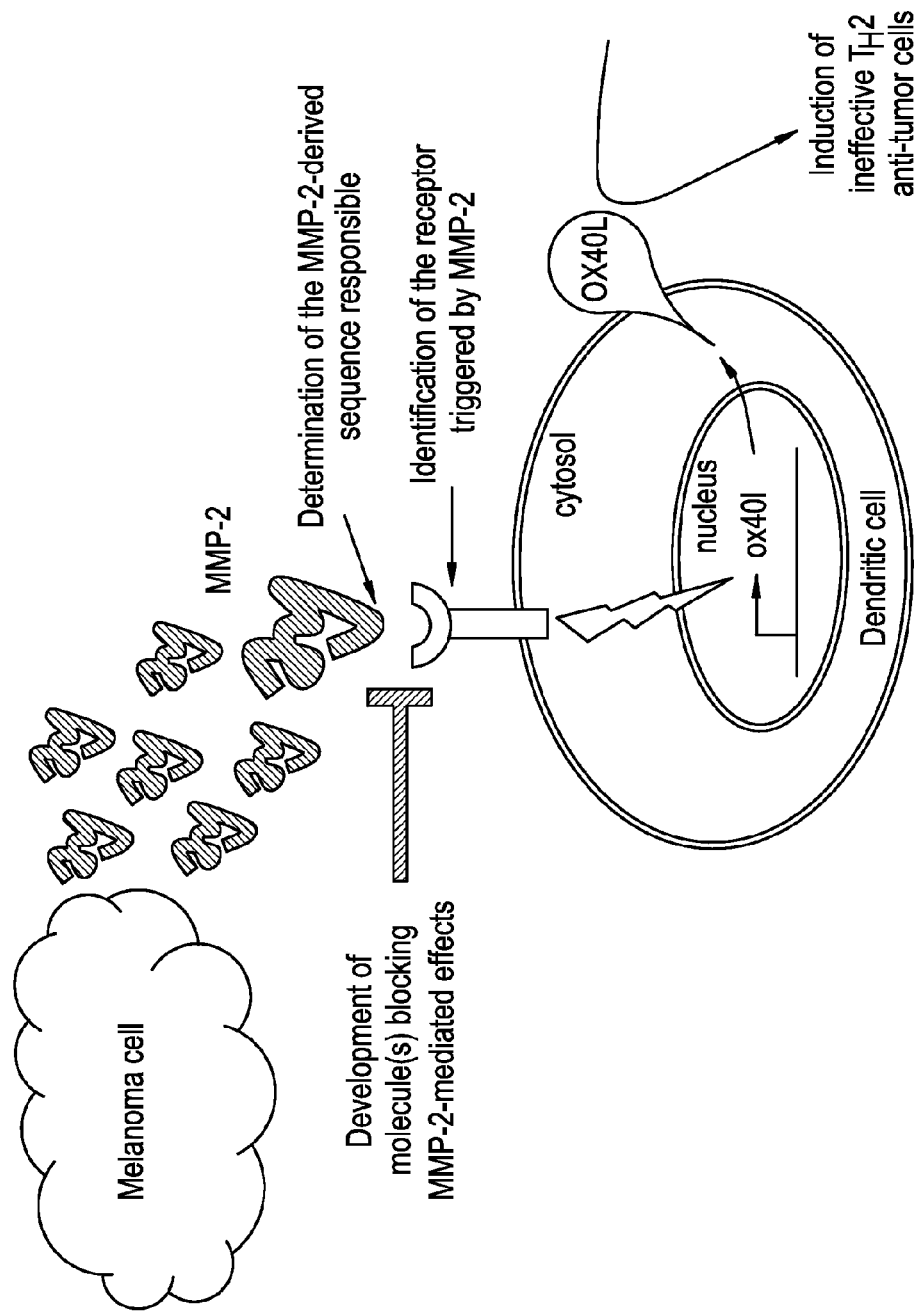

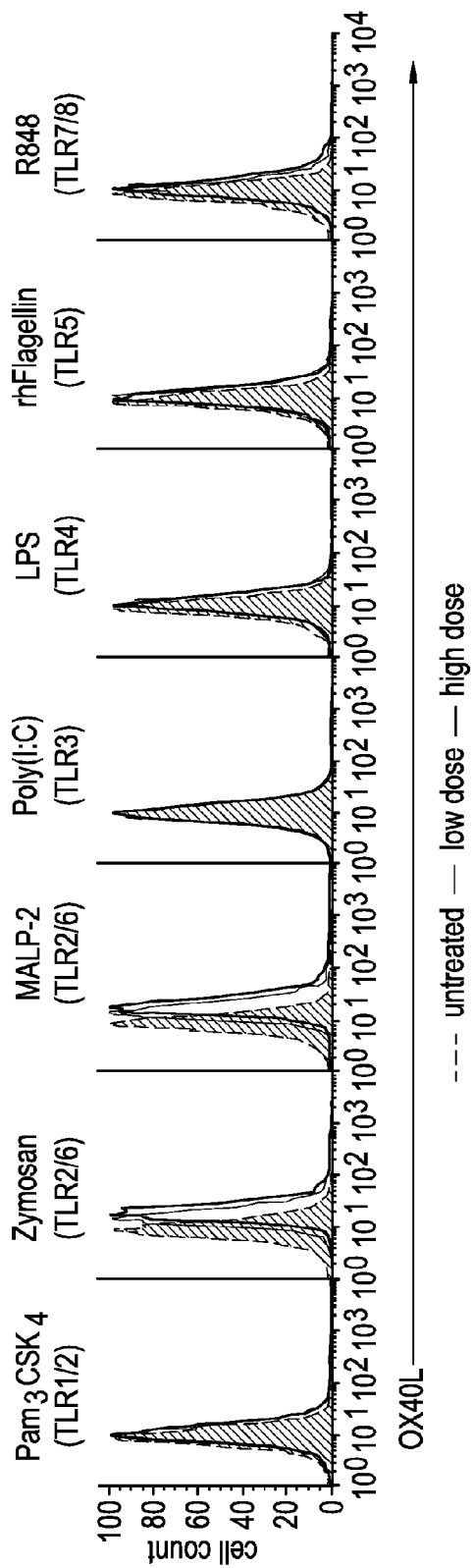
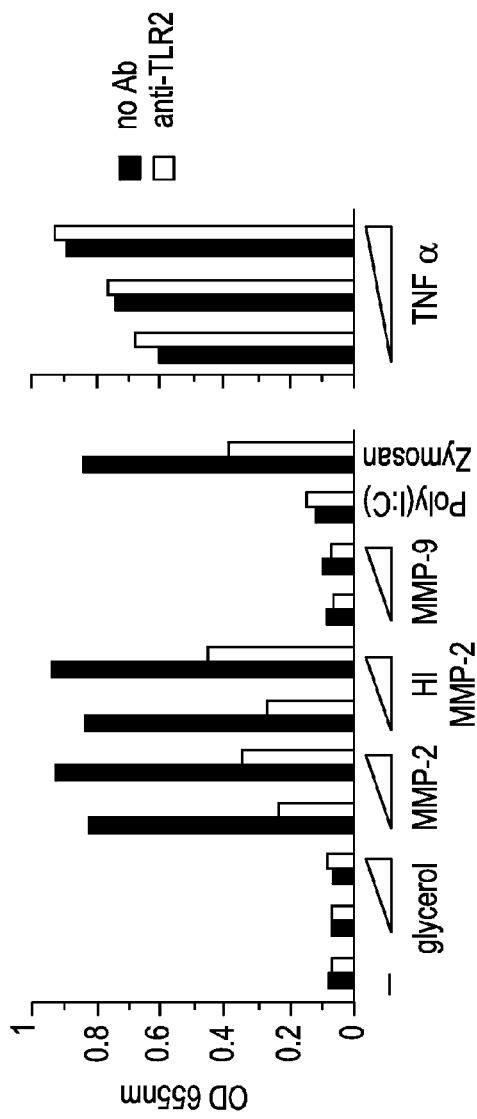
FIG. 4A
FIG. 4B

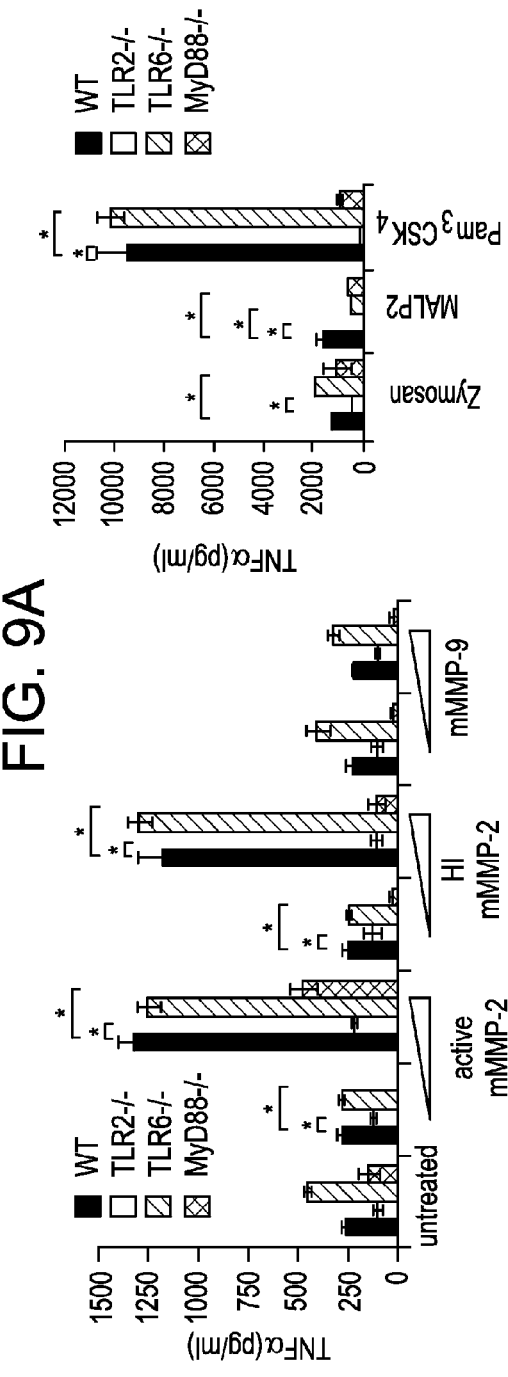
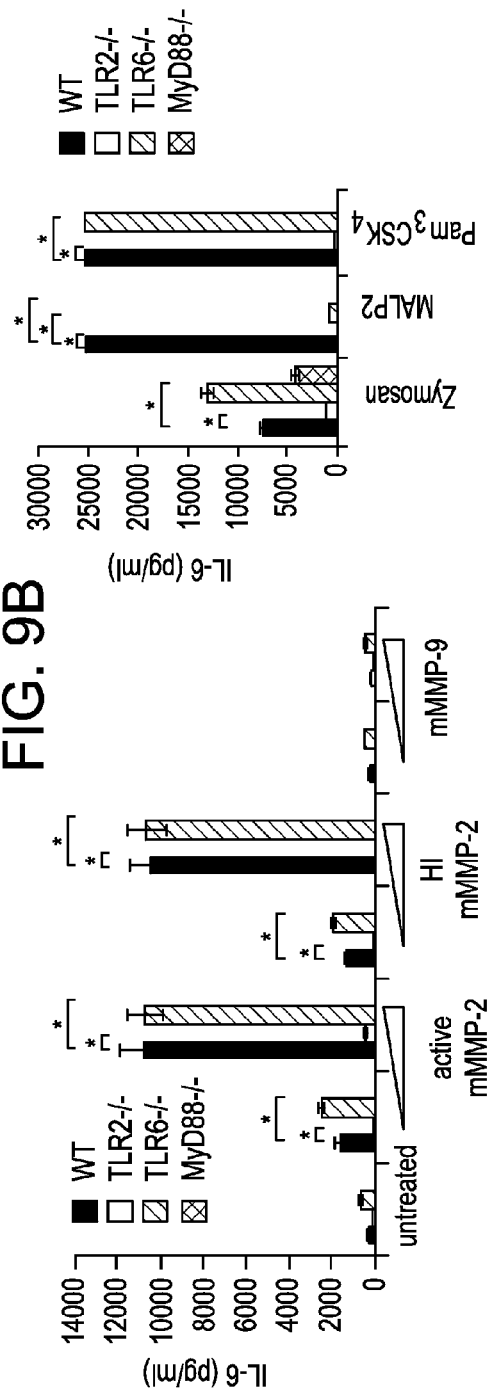
FIG. 9A
FIG. 9B

METHODS, AGENTS AND PEPTIDES FOR INHIBITING MATRIX METALLOPROTEINASE-2 SIGNALING

CROSS REFERENCE TO RELATED APPLICATIONS

The present application is a National Stage Application which claims priority under 35 U.S.C. §120 from co-pending PCT Application No. PCT/US2012/054380 filed Sep. 10, 2012, which in turn claims priority under 35 U.S.C. §119(e) from U.S. Provisional Application Ser. No. 61/573,542, filed Sep. 8, 2011, each of which applications are herein specifically incorporated by reference in their entireties.

GOVERNMENTAL SUPPORT

The research leading to the present invention was supported, at least in part, by National Institutes of Health Grant Nos. R01 AI071078 and 1R01AI061684. Accordingly, the Government has certain rights in the invention.

FIELD OF THE INVENTION

The present invention relates to methods for screening to identify modulator agents or compounds that affect matrix metalloproteinase-2 (MMP-2) mediated activation of toll-like receptor-2 (TLR-2). Also encompassed herein are methods for modulating MMP-2 mediated activation of TLR-2 and to the application of MMP-2 peptides for pharmaceutical and immunogenic compositions, as well as vaccines. Pharmaceutical and immunogenic compositions comprising agents or compounds that modulate MMP-2 mediated activation of TLR-2 are also encompassed herein. Melanoma is an exemplary tumor type that expresses MMP-2 and for which such pharmaceutical and immunogenic compositions, as well as vaccines, would confer benefit to patients. The invention further relates to methods and means to reduce or inhibit MMP-2 mediated activation of TLR-2 and downstream signaling therefrom so as to achieve a more effective T cell response to MMP-2 expressing tumors.

BACKGROUND OF THE INVENTION

The citation of references herein shall not be construed as an admission that such is prior art to the present invention.

A large array of human melanoma-associated antigens (MAA) has been identified and used in various immunization strategies to treat cancer patients. However, despite significant induction of tumor-specific T cells (Coulie and van der Bruggen, 2003; Rosenberg, 2004), the therapeutic efficacy of these approaches has been suboptimal, indicating a need for improving current strategies. Possible explanations for failure (Loose and Van de Wiele, 2009) include malignant cells producing immunosuppressive cytokines (IL-10, TGFβ, IL-6 and M-CSF), prostaglandins and vascular endothelial growth factor, thereby skewing the immune response towards type-2 or regulatory T cells and deleteriously modulating the differentiation, maturation and function of antigen presenting cells (APCs). Furthermore, malignant cells that chronically stimulate infiltrating T cells can actively exhaust and eliminate T cells through expression of molecules such as FasL, PDL-1 or RCAS 1. Finally, due to immune pressure, immunoresistant tumor cell variants emerge through selection of mutants with reduced antigenicity. This can affect the expression/function of molecules implicated in antigen processing and presentation or the expression of tumor antigens themselves (Hirohashi et al., 2009; Yee et al., 2000).

A way to circumvent this latter limitation would be to vaccinate against immunogenic proteins whose expression is critical for tumor growth and/or invasiveness. The matrix metalloproteinase-2 (MMP-2), overexpressed in many tumors including melanoma, may be such an antigen. MMP-2 is a proteolytic enzyme that degrades numerous components of extracellular matrix such as collagens, laminin or fibronectin and contributes to cell migration by clearing the surrounding extracellular matrix and basement membrane barriers. MMP-2 over-expression has been associated with tumor progression. Indeed, MMP-2 modulates various oncogenic processes such as angiogenesis (Brooks et al., 1998; Itoh et al., 1998) and tumor dissemination (Kessenbrock et al., 2010; Liotta et al., 1980; Westermarck and Kahari, 1999).

The present inventors previously identified MMP-2 as a novel melanoma-associated antigen (MAA) recognized by HLA-A*0201-restricted CD8$^+$ tumor infiltrating lymphocytes (TILs) (Godefroy et al., 2005). Because MMP-2 activity is critical for melanoma progression, MMP-2 is a promising tumor antigen to target in immunotherapy against malignant melanoma. Accordingly, several patients administered CD8$^+$ T cells that recognize this epitope among others have remained tumor-free up to 15 years after treatment (Godefroy et al., 2005; Khammari et al., 2007).

SUMMARY OF THE INVENTION

The invention relates generally to methods and agents for inducing an effective immune response to melanoma and other tumors that express MMP-2. Several melanoma-associated antigens have been targeted in immunization strategies to treat melanoma patients. The therapeutic efficacy of these approaches remains limited, however, indicating an urgent need for improved strategies. Because MMP-2 activity is critical for progression of many tumors, including that of melanoma, it represents an interesting target for vaccine therapy. MMP-2 is an immunogenic tumor antigen. MMP-2-specific CD4$^+$ T lymphocytes, however, display a suboptimal inflammatory $T_H2$ profile. As shown herein, MMP-2-specific skewing toward a $T_H2$ profile is driven, at least in part, by MMP-2 mediated activation of TLR-2. Elucidation of modulators of TLR-2/MMP-2 interaction and therapeutic use thereof will, therefore, lead to improved immune responses comprising more effective $T_H1$ responses in patients. The findings presented herein underscore the potential for targeting TLR-2/MMP-2 interaction in the development of therapeutics for melanoma and other tumors that express MMP-2.

Accordingly, a method for screening to identify a modulator of matrix metalloproteinase-2 (MMP-2) mediated activation of toll-like receptor-2 (TLR-2) is presented herein, the method comprising: contacting a composition comprising TLR-2 and MMP-2 with a candidate modulator agent and assessing TLR-2/MMP-2 interaction levels in the presence of the candidate modulator agent, wherein detecting a change in TLR-2/MMP-2 interaction levels in the presence of the candidate modulator agent relative to TLR-2/MMP-2 interaction levels in the presence of a control agent identifies a modulator of MMP-2 mediated activation of TLR-2. In a particular embodiment thereof, the change detected in the presence of the candidate modulator agent is a reduction in TLR-2/MMP-2 interaction levels, thereby identifying the candidate modulator agent as an inhibitor of MMP-2 mediated activation of TLR-2.

In an aspect of the method, the TLR-2 is expressed on a cell. In a particular embodiment thereof, the cell is transfected to express TLR-2. Accordingly, a cell expressing endogenous or exogenous TLR-2 is contacted with the MMP-2.

In an embodiment of the method, the change in TLR-2/MMP-2 interaction levels is detected by measuring nuclear factor-κB (NF-κB) signaling, secretion of inflammatory cytokines, or OX40 ligand (OX40L) expression on the cell. In a more particular aspect, the change detected in the presence of the candidate modulator agent is a reduction in nuclear factor-κB (NF-κB) signaling, secretion of inflammatory cytokines, or OX40 ligand (OX40L) expression on the cell.

In a further aspect, the TLR-2 is an isolated protein and the TLR-2 is contacted with MMP-2. In a particular embodiment, the MMP-2 is an isolated protein.

In a particular aspect, the candidate modulator agent is a small organic molecule, a protein or peptide, a nucleic acid, a carbohydrate, or an antibody. Also encompassed are compositions comprising modulator agents identified using the screening assays described herein and a pharmaceutically acceptable carrier. Methods for using modulator agents identified using the screening assays described herein and compositions thereof for the treatment of patients afflicted with MMP-2 expressing tumors are also envisioned. In an aspect thereof, the MMP-2 expressing tumor is melanoma, breast cancer, colon cancer, gastric cancer, lung cancer, ovarian cancer, pancreatic cancer, prostate cancer, squamous cell carcinoma of the head and neck, non-skull base chroma bone tumors, follicular thyroid carcinoma, or bladder cancer.

Also encompassed herein is an MMP-2 peptide, wherein the MMP-2 peptide consists of 40-50 contiguous amino acids of SEQ ID NO: 1 or is at least 90% identical to any one of the MMP-2 peptides of 40-50 contiguous amino acids of SEQ ID NO: 1. In a more particular embodiment, the MMP-2 peptide consisting of 40-50 contiguous amino acids of SEQ ID NO: 1 comprises at least two of P1-20, P11-30, P21-40, P41-60, P161-180, P361-380, P551-570, P571-590, P601-620, P621-640, or P631-650 of SEQ ID NO: 1; or is at least 90% identical to any one of the MMP-2 peptides of 40-50 contiguous amino acids of SEQ ID NO: 1 comprising at least two of P1-20, P11-30, P21-40, P41-60, P161-180, P361-380, P551-570, P571-590, P601-620, P621-640, or P631-650 of SEQ ID NO: 1, wherein the MMP-2 peptide comprises a CD4+ T cell epitope. As is understood in the art, at least 90% identical encompasses at least 90%, at least 91%, at least 92%, at least 93%, at least 94%, at least 95%, least 96%, at least 97%, at least 98%, and at least 99% identical.

In a particular embodiment, the MMP-2 peptide consists of at least two of P1-20, P11-30, P21-40, P41-60, P161-180, P361-380, P551-570, P571-590, P601-620, P621-640, or P631-650 of SEQ ID NO: 1, or is at least 90% identical to the MMP-2 peptide consisting of at least two of P1-20, P11-30, P21-40, P41-60, P161-180, P361-380, P551-570, P571-590, P601-620, P621-640, or P631-650 of SEQ ID NO: 1.

In another embodiment, the MMP-2 peptide consists of the amino terminal two-thirds of SEQ ID NO: 1. In a particular embodiment thereof, the MMP-2 peptide consists of amino acids 1-445 of SEQ ID NO: 1. Smaller fragments of the MMP-2 peptide consisting of amino acids 1-445 of SEQ ID NO: 1 are, furthermore, envisioned and encompassed herein.

Also encompassed herein are vaccine or immunogenic compositions comprising a pharmaceutically acceptable carrier and at least one of the MMP-2 peptides described herein.

In another aspect, a method for stimulating or enhancing an immune response to a matrix metalloproteinase-2 (MMP-2) expressing tumor comprising administering at least one of the MMP-2 peptides described herein, or a nucleic acid sequence encoding same; or a vaccine or immunogenic composition described herein to a subject in need thereof is elucidated herein. In an aspect thereof, the MMP-2 expressing tumor is melanoma, breast cancer, colon cancer, gastric cancer, lung cancer, ovarian cancer, pancreatic cancer, prostate cancer, squamous cell carcinoma of the head and neck, non-skull base chroma bone tumors, follicular thyroid carcinoma, or bladder cancer.

The peptides described herein may be is associated with or covalently attached to a polycationic or cell penetrating peptide to promote cellular uptake or delivery. More particularly, the polycationic or cell penetrating peptide is a Tat peptide comprising the sequence RKKRRQRRR (SEQ ID NO: 25).

Methods described herein may further comprise assessing enhanced cell mediated and/or humoral immune responses, wherein enhanced cell mediated immune responses are detected as an increase in at least one of MMP-2-specific CD4+ $T_H1$ cells, MMP-2-specific CD8+ T cells, and dendritic cells expressing type-I IFN receptor (IFNAR1); or a decrease in OX40L expression or NF-κB activity in dendritic cells; and enhanced humoral immune responses are detected as an increase in at least one of MMP-2 specific B cells and MMP-2 specific antibodies.

In a particular embodiment, the subject in need thereof is a mammalian subject. More particularly, the mammalian subject is a human. In a more particular embodiment, the mammalian subject has an MMP-2 expressing tumor. Melanoma is an exemplary MMP-2 expressing tumor.

Other objects and advantages will become apparent to those skilled in the art from a review of the ensuing detailed description, which proceeds with reference to the following illustrative drawings, and the attendant claims.

BRIEF DESCRIPTION OF THE DRAWINGS

FIG. 1 shows a cartoon depicting the effect of tumor derived MMP-2 on dendritic cells and consequences thereof, as well as targets for screening assays to identify therapeutic agents.

FIGS. 4A-B shows that MMP-2 activates the NF-κB pathway through TLR-2 triggering. A) DCs were exposed to various TLR agonists for 2 days before cells were stained for OX40L. Zymosan and MALP-2, two TLR2/6 agonists induce OX40L on DCs. B) TLR2-transfected and engineered HEK cells were incubated with MMP-2 (5 mg/ml) or various controls. All conditions were also tested in the presence of a blocking antibody for TLR2. TNFα was used to activate NF-κB in a TLR-independent manner. Twenty hours later, NF-κB activation was measured. MMP-2 and the TLR2-agonist zymosan activate NF-κB in a TLR2-dependent manner.

DETAILED DESCRIPTION

Melanoma cells are highly resistant to traditional treatments such as chemotherapy and radiotherapy. On the other hand, they are quite immunogenic and therefore a lot of effort has been put into developing immune therapies to treat cancer patients. So far, these therapeutic strategies have achieved little clinical effect, despite generating detectable immune responses. The tumor microenvironment is believed to be responsible for these failures by locally blocking anti-tumor immune responses and therefore allowing tumor cells to escape the immune system. MMP-2 is over-expressed in several cancers including melanoma, and its expression is associated with increased dissemination and poorer survival/prognosis [Egeblad et al. *Nat Rev Cancer* 2, 161-174, (2002); Hofmann et al. *J Invest Dermatol* 115, 337-344, (2000)]. MMP-2, therefore, represents a key player in immune escape of tumor cells and its pro-tumoral functions make it an appealing target for cancer therapy. The present inventors have found that MMP-2-conditioned dendritic cells (DCs) preferentially generate $T_H2$ cells through a mechanism involving OX40L expression [Godefroy et al. *Cancer Cell* 19, 333-346, (2011)]. MMP-2, therefore, acts as an endogenous $T_H2$ "conditioner" and may underlie the prevalence of detrimental $T_H2$ responses in melanoma.

As described herein, the present inventors have elucidated the mechanism underlying MMP-2-induction of OX40L expression on DCs and identified TLR-2 as a critical player in this process. Further to the discovery of MMP-2 mediated activation of TLR-2, which leads to OX40L expression on DCs, the present inventors have developed a screening assay to identify agents/molecules capable of modulating MMP-2/TLR-2 interaction. In a particular embodiment, screening assays directed to identifying agents/molecules capable of blocking the MMP-2 signaling (i.e., inhibitors thereof) leading to OX40L expression and subsequent generation of detrimental anti-tumor $T_H2$ cells (FIG. 1) are envisioned. Such screening assays may, for example, be cell based assays that utilize cells that express endogenous TLR-2 or are transfected to express exogenous TLR-2 or may be performed with compositions comprising isolated TLR-2 and MMP-2.

Figure 2A:
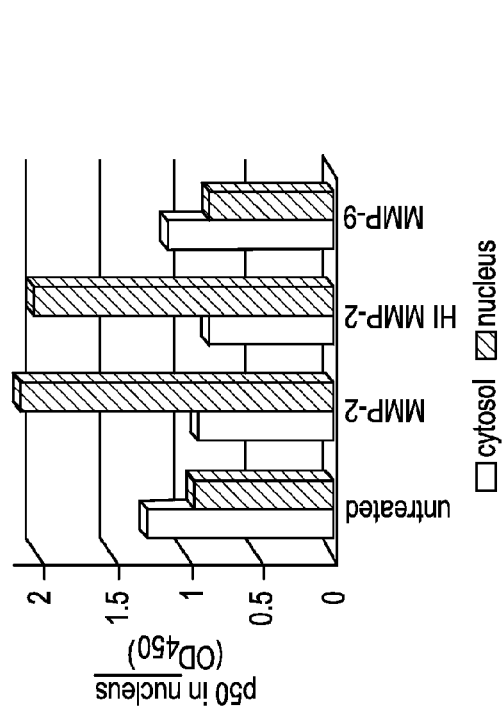
FIG. 2A-C shows that MMP-2 activates the NF-κB pathway. A) DCs were exposed to MMP-2 (5 μm/ml) or zymosan (10 μm/ml), a known activator of NF-κB that acts via TLR2, for the indicated time. Cytosolic and nuclear fractions were isolated and p50 contents were measured by ELISA. MMP-2 and zymosan induce p50 translocation in the nucleus after 30 min. B) Active and heat-inactivated (HI) MMP-2, but not MMP-9, trigger p50 translocation in the nucleus. C) OX40L over-expression on DCs induced by MMP-2 is inhibited by an inhibitor of NEMO, the NEMO binding domain (NBD) peptide, but not by the corresponding negative control, a NBD mutant.

More particularly, and as set forth herein in greater detail in the Examples and Drawings, the present inventors investigated whether MMP-2 could activate the NF-κB pathway. This experimental course was suggested by the presence of two atypical NF-κB binding sites in the promoter region of the ox40l gene [Arima et al. *Sci Signal* 3, (2010)]. Results presented herein demonstrate that MMP-2 triggers two components of the NF-κB pathway as reflected by p50 translocation into the nucleus (FIGS. 2A-B) and NEMO activation (FIG. 2C). MMP-2-treated DCs also secrete a spectrum of inflammatory cytokines, including IL-1β, IL-6, IL-8, TNFα, which are known to be under the control of NF-κB (FIG. 2D). In sum, the results presented in FIG. 2 show that MMP-2 activates the NF-κB pathway in DCs.

To explore further the mechanism whereby MMP-2 activates NF-κB, the present inventors used TLR-transfected engineered HEK cells as reporter cell lines. In so doing, the present inventors discovered that MMP-2 activates NF-κB through TLR-2 triggering (FIG. 4). TLR-2 often forms dimers with TLR-1 or TLR-6, which increases the spectrum of ligands. Preliminary data suggest that MMP-2 triggers TLR-2 independently of TLR-1 and TLR-6. Indeed, a blocking antibody for TLR-6 did not affect TLR-2 triggering by MMP-2. Additionally, TLR-2/TLR-1 agonists such as Pam3CSK4 did not induce OX40L over-expression on either TLR-2-transfected HEK cells or DCs. See FIG. 7. Accordingly, TLR-2 transfected engineered HEK reporter cell lines are set forth as an exemplary component of a cell based screening assay to identify modulators of MMP-2/TLR-2 interaction. Modulators identified using TLR-2 transfected engineered HEK reporter cells or other TLR-2 transfected engineered reporter lines having similar properties can be tested on DCs (DCs that express endogenous TLR-2 or are engineered to express exogenous TLR-2) to confirm inhibition of TLR-2 triggering in a DC cellular context. In addition, negative control cell lines, such as, for example, the parental engineered HEK reporter cells (TLR-2 negative) will be included in any experimental studies.

Figure 2B:
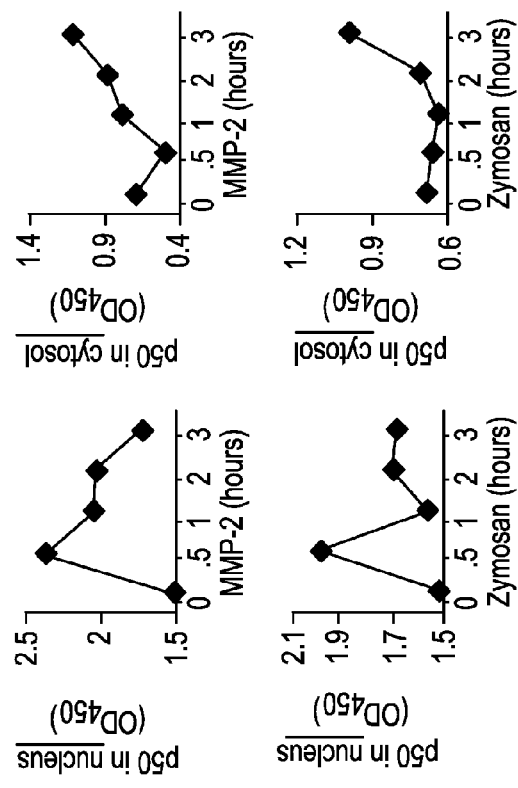
Figure 2C:
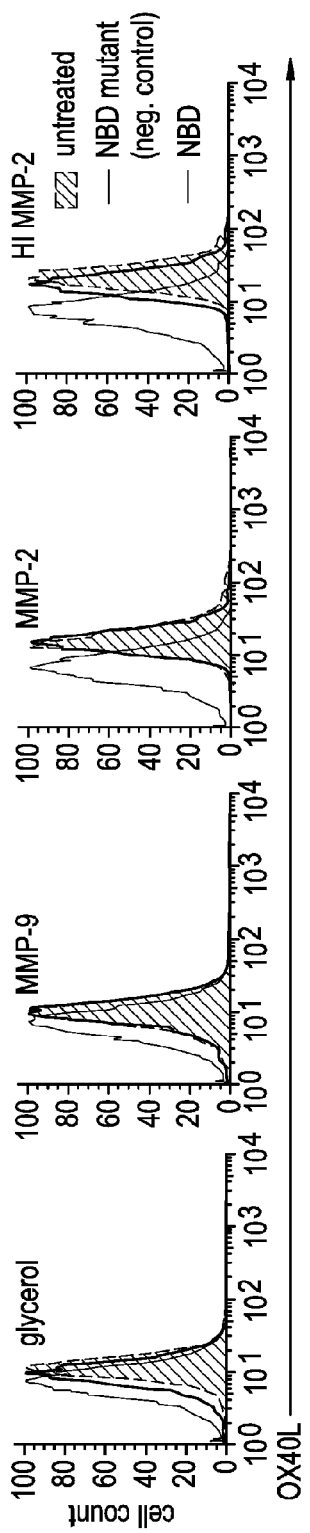
Figure 3:
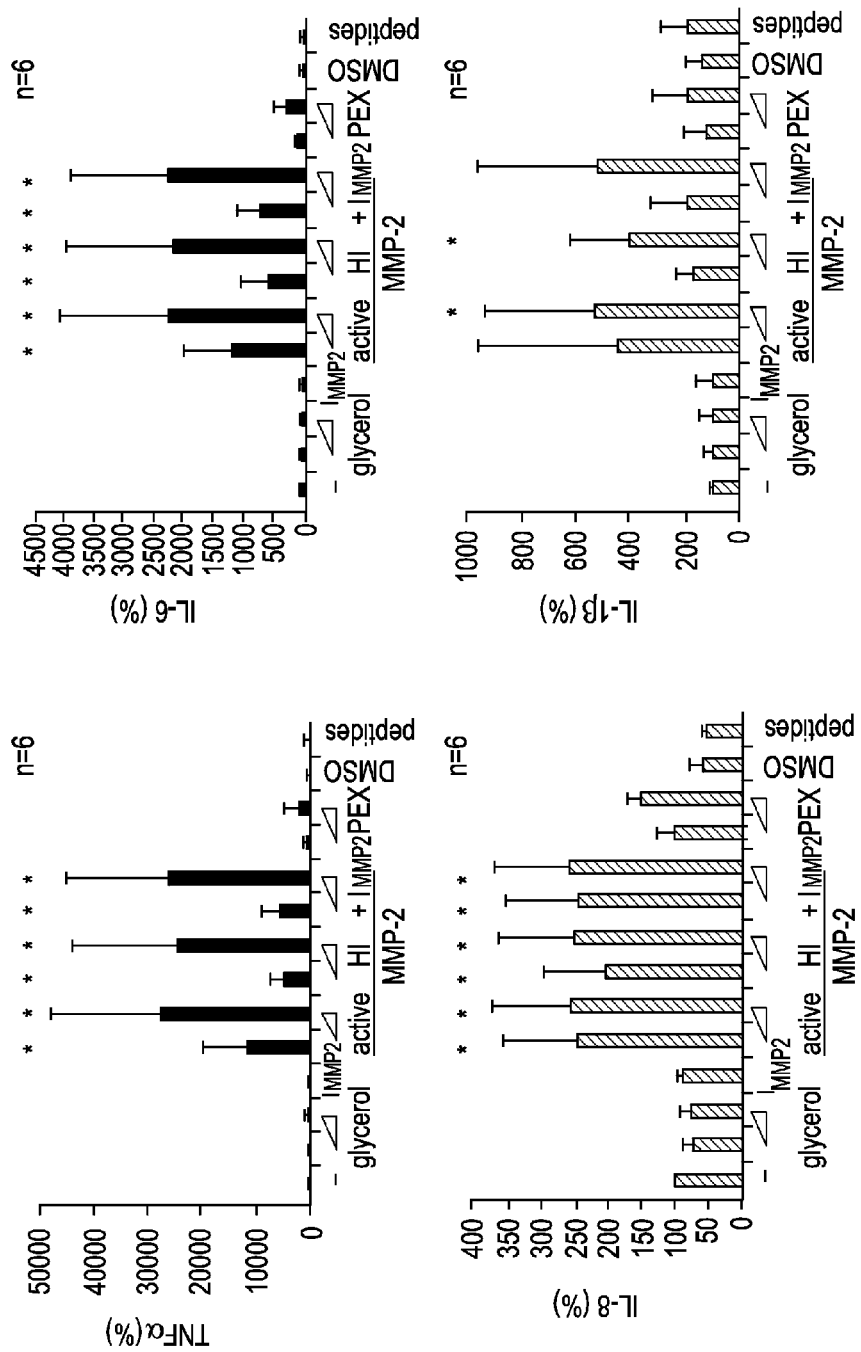
FIG. 3 shows that MMP-2 induces DCs to secrete inflammatory cytokines. DCs were exposed to MMP-2 (0.5 and 5 mg/ml) in various forms: active, heat-inactivated (HI), inhibited by a specific inhibitor ($I_{MMP-2}$), PEX (last third of MMP-2, amino acids 445-635 of SEQ ID NO: 1), overlapping peptides (20-mer) spanning MMP-2, or controls. Eighteen hours later, supernatants were harvested and TNFα, IL-6, IL-8 and IL-β levels were measured by cytokine bead array. Inflammatory cytokine were significantly expressed by DCs exposed to MMP-2 (active or inactive). *p<0.05, two-tailed paired Student t-test.
Figure 5:
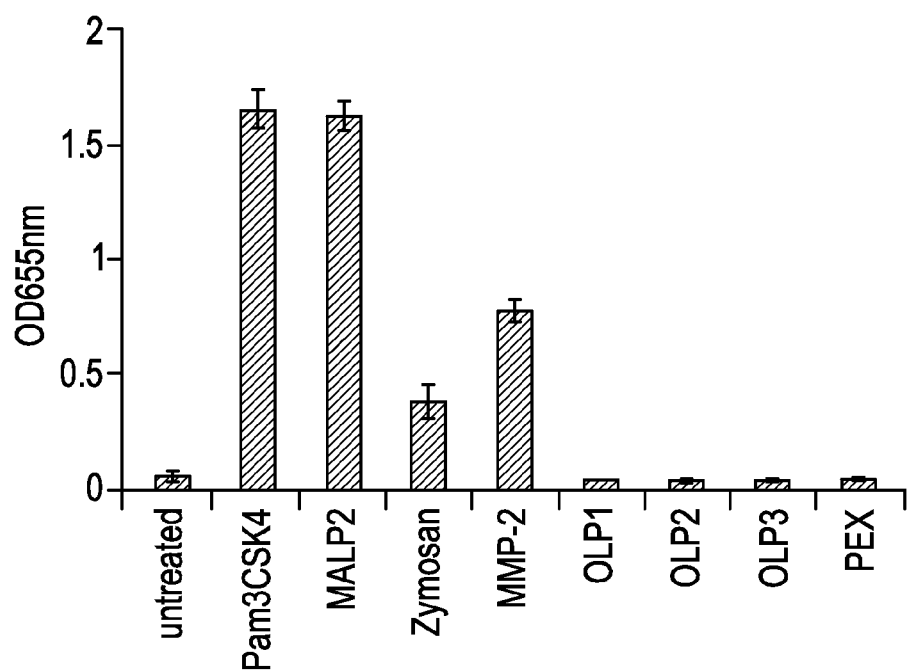
FIG. 5 shows that overlapping 20-mers spanning MMP-2 and PEX, the C-terminal third of MMP-2 do not trigger TLR2. TLR2-transfected and engineered HEK cells were incubated with MMP-2 (5 mg/ml), TLR2 agonists, recombinant PEX and 3 pools of overlapping 20-mers covering MMP-2. OLP1: mix of 22 overlapping peptides covering MMP-2 from amino-acid 1 to 220; OLP2: mix of 22 overlapping peptides covering MMP-2 from amino-acid 210 to 440; OLP3: mix of 22 overlapping peptides covering MMP-2 from amino-acid 450 to 660. Twenty hours later, NF-κB activation was measured. Neither PEX nor the peptides triggered NF-κB signaling.
Figure 6:
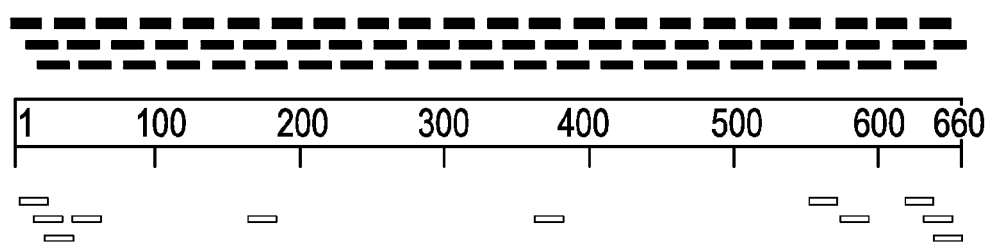
FIG. 6 shows MMP-2 peptides/epitopes. A) MMP-2 protein (660 amino acid-long) is represented in gray. Overlapping peptides spanning the entire MMP-2 amino acid sequence and used in the present study are represented in black. MMP-2 epitopes recognized by CD4+ T cell clones are shown in light gray.

As shown in FIGS. 2 and 3, both active MMP-2 and heat-inactivated (HI) MMP-2 induce OX40L expression (FIG. 2C) and NF-κB activation (FIGS. 2A, 2B and 3) at similar levels in DCs, demonstrating that MMP-2 protein conformation is not key for TLR-2 triggering/binding. As suggested by results presented in FIG. 5, the minimal MMP-2 peptide sequence needed for TLR-2 triggering/binding appears to be over 20 amino acids long and is likely to be located in the first two-thirds of MMP-2. See additional details presented herein below and FIG. 6 for information pertaining to the MMP-2 20-mers tested in pools and assayed as shown in FIG. 5.

Further to the objective of delineating MMP-2 peptide sequences involved in TLR-2 triggering/binding, the present inventors are generating various recombinant fragments of MMP-2 and testing their ability to induce OX40L expression and NF-κB activation in DCs as well as in TLR-2-transfected HEK cells. Such fragments will serve to identify sub-fragments of MMP-2 that retain the ability of full length MMP-2 to activate TLR-2, as assayed by increased TLR-2 signaling, NF-κB activation and OX40L expression. Exemplary MMP-2 fragments comprise or consist of at least two of 20-mer MMP-2 peptides described herein or consist of the amino terminal two-thirds of full length MMP-2. See additional details presented herein below and FIG. 6 for information pertaining to the MMP-2 20-mers.

Exploiting a high throughput screening method using, for example, TLR-2-transfected engineered HEK cells, small MMP-2 peptides located in the minimal MMP-2 sequence responsible for TLR-2 triggering will be screened for their ability to block signaling. Since the three dimensional structures of MMP-2 and TLR2 are known, three dimensional modeling can also be used to design small molecules with the capacity to prevent MMP-2/TLR2 interaction/binding. Candidate molecules generated based on three dimensional structures can, for example, be tested using TLR-2-transfected HEK cells. The level of inhibition of NF-κB, OX40L and subsequent $T_H2$ immune responses will also be assessed in the presence of any small molecule identified using the screening assays described herein. T cells generated in the presence of small inhibitor molecules are expected to display a $T_H1$ phenotype, i.e. secreting anti-tumoral IFNγ and exhibiting tumor cell targeted cytolytic activity.

With respect to the MMP-2 20-mers described herein, the present inventors generated a library of overlapping peptides covering the entire sequence of MMP-2 (SEQ ID NO: 1). See FIG. 6 for a schematic which depicts the library of overlapping peptides and the relative positions of the 11 MMP-2-derived peptides recognized by CD4+ T cell clones. Amino and nucleic acid sequences for the MMP-2 20-mers are presented herein below. Amino and nucleic acid sequences corresponding to 40-50-mers of contiguous MMP-2 sequence are readily understood and envisioned based on SEQ ID NOs: 1 and 13. A 40-mer of SEQ ID NO: 1 may, for example, span amino acids 1-40; 10-50; 20-60; 30-70; or 40-80 and so on to the carboxy terminus of SEQ ID NO: 1. A 50-mer of SEQ ID NO: 1 may, for example, span amino acids 1-50; 10-60; 20-70; 30-80; or 40-90 and so on to the carboxy terminus of SEQ ID NO: 1.

The MMP-2 protein sequence (from amino to carboxy termini) is presented in SEQ ID NO: 1 of the Sequence Listing.

The MMP-2 nucleic acid sequence is presented in SEQ ID NO: 13 of the Sequence Listing.

By way of background, the present inventors used a pool of sixty-six 20-amino acid long, partially overlapping peptides spanning the entire sequence of MMP-2 (SEQ ID NO: 1) to screen for the presence of MMP-2-specific CD4+ T cells and identify the specific MMP-2 epitopes for which these clones were specific. See, for example, FIG. 6. Using this method, CD4+ T cell clones specific for eleven distinct and novel MMP-2-derived peptides/epitopes were generated. An empirical approach to determining which, if any, of the potential MMP-2 peptides could induce MMP-2-specific CD4+ T cells was necessitated because of the nature and complexity of antigen processing and presentation by antigen presenting cells [APCs; e.g., monocyte-derived dendritic cells (DCs)] and the additional complexities involved in T cell recognition of presented antigen, which are influenced by, for example, the presence and/or concentration of particular cytokines that are instructive for divergent T cell differentiation pathways.

With regard to antigen presentation, proteins are engulfed by APCs and peptides are generated therefrom after cleavage and trimming of the protein by various proteases and peptidases localized in different subcellular compartments or the cytoplasm. This processing step leads to expression of the produced peptides on the APC surface via presentation on one of the highly polymorphic class-II HLA molecules. Peptide-HLA complexes can subsequently be recognized by particular T cells via T cell receptors (TCR), which exhibit exquisite antigen specificity. Because each step of the processes briefly described above involves so many known and unknown variables, epitopes that are going to be processed, presented and recognized by T cells cannot be predicted. In light of the above, a TCR epitope can only be identified experimentally via exhaustive analyses such as those described herein for MMP-2.

The relative positions within full length MMP-2 and amino acid sequences of the 11 novel MMP-2-derived peptides identified as specific epitopes recognized by CD4+ T cell clones and nucleic acid sequences encoding same are as follows:

```
P1-20:
                                         (SEQ ID NO: 2)
MEALMARGALTGPLRALCLL, encoded by
                                         (SEQ ID NO: 14)
atg gag gcg cta atg gcc cgg ggc gcg ctc acg ggt ccc ctg agg gcg ctc tgt ctc ctg;

P11-30:
                                         (SEQ ID NO: 3)
TGPLRALCLLGCLLSHAAAA, encoded by
                                         (SEQ ID NO: 15)
acg ggt ccc ctg agg gcg ctc tgt ctc ctg ggc tgc ctg ctg agc cac gcc gcc gcc gcg;
```

-continued

P21-40:
(SEQ ID NO: 4)
GCLLSHAAAAPSPIIKFPGD, encoded by
(SEQ ID NO: 16)
ggc tgc ctg ctg agc cac gcc gcc gcc gcg ccg tcg ccc atc atc aag ttc ccc ggc gat;

P41-60:
(SEQ ID NO: 5)
VAPKTDKELAVQYLNTFYGC, encoded by
(SEQ ID NO: 17)
gtc gcc ccc aaa acg gac aaa gag ttg gca gtg caa tac ctg aac acc ttc tat ggc tgc;

P161-180:
(SEQ ID NO: 6)
RIHDGEADIMINFGRWEHGD, encoded by
(SEQ ID NO: 18)
cga atc cat gat gga gag gca gac atc atg atc aac ttt ggc cgc tgg gag cat ggc gat;

P361-380:
(SEQ ID NO: 7)
ESCTSAGRSDGKMWCATTAN, encoded by
(SEQ ID NO: 19)
gag agc tgc acc agc gcc ggc cgc agt gac gga aag atg tgg tgt gcg acc aca gcc aac;

P551-570:
(SEQ ID NO: 8)
GYPKPLTSLGLPPDVQRVDA, encoded by
(SEQ ID NO: 20)
ggg tac ccc aag cca ctg acc agc ctg gga ctg ccc cct gat gtc cag cga gtg gat gcc;

P571-590:
(SEQ ID NO: 9)
AFNWSKNKKTYIFAGDKFWR, encoded by
(SEQ ID NO: 21)
gcc ttt aac tgg agc aaa aac aag aag aca tac atc ttt gct gga gac aaa ttc tgg aga;

P601-620:
(SEQ ID NO: 10)
GFPKLIADAWNAIPDNLDAV, encoded by
(SEQ ID NO: 22)
ggc ttt ccc aag ctc atc gca gat gcc tgg aat gcc atc ccc gat aac ctg gat gcc gtc;

P621-640:
(SEQ ID NO: 11)
VDLQGGGHSYFFKGAYYLKL, encoded by
(SEQ ID NO: 23)
gtg gac ctg cag ggc ggc ggt cac agc tac ttc ttc aag ggt gcc tat tac ctg aag ctg;
and

P631-650:
(SEQ ID NO: 12)
FFKGAYYLKLENQSLKSVKF, encoded by
(SEQ ID NO: 24)
ttc ttc aag ggt gcc tat tac ctg aag ctg gag aac caa agt ctg aag agc gtg aag ttt.

Upon antigen stimulation, the MMP-2 specific CD4+ T cell clones identified secreted inflammatory $T_H2$ cytokines, i.e. TNFα, IL-4 and IL-13, but no or little IFNγ and IL-2. Further analyses revealed that MMP-2 drives the differentiation of $T_H2$ responses through inhibition of IL-12p70 production and OX40L expression by DCs. These findings demonstrate that MMP-2 polarizes naive CD4+ T cells towards an inflammatory $T_H2$ profile, thereby limiting effective antitumor T cell responses.

As described herein for the first time, TLR-2 has been identified as a critical component of the signaling machinery underlying MMP-2-induction of OX40L expression on DCs. Further to the discovery of MMP-2 mediated activation of TLR-2, which leads to OX40L expression on DCs, the present inventors have developed screening assays to identify agents/molecules capable of modulating MMP-2/TLR-2 interaction. Such screening assays, which are based on a mechanistic understanding of MMP-2 mediated activation of TLR-2, provide systems for identifying novel therapeutic agents and developing strategies to modulate immune responses qualitatively to either induce the generation of $T_H2$ cells in patients in need thereof, such as patients with auto-immune diseases, or block the generation of $T_H2$ cells in patients in need thereof, such as cancer patients.

In a particular embodiment, screening assays directed to identifying agents/molecules capable of blocking MMP-2-dependent TLR-2 signaling (i.e., inhibitors thereof) leading to OX40L expression and subsequent generation of detrimental anti-tumor $T_H2$ cells (FIG. 1) are described. Such screening assays may, for example, be cell based assays that utilize cells that express endogenous TLR-2 or are transfected to express exogenous TLR-2 or may be performed with compositions comprising isolated TLR-2 and MMP-2. TLR-2-transfected (stably) HEK-Blue™ Cells represent a very efficient high throughput reagent for screening due to an easy read-out. Indeed, HEK-Blue™-hTLR2 Cells are specifically designed for studying the stimulation of human TLR-2 by monitoring the activation of NF-κB. HEK-Blue™-hTLR2 Cells were obtained by co-transfection of the hTLR2 and SEAP (secreted embryonic alkaline phosphatase) reporter genes into HEK293 cells. The SEAP reporter gene is placed under the control of NF-κB-binding sites. Stimulation with a TLR2 ligand activates NF-κB which induces the production of SEAP. Levels of SEAP can be readily determined with QUANTI-Blue™, a detection medium that turns purple/blue in the presence of alkaline phosphatase. HEK-Blue™-hTLR2 Cells can be incubated with MMP-2 in the presence of candidate agents/molecules. Inhibition of NF-κB activation by any agents/molecules can be assessed and confirmed in DCs (which endogenously express TLR2 or are engineered to express exogenous TLR2) in order to corroborate the initial screening results in a native or more natural context. Additionally, agents/molecules identified as inhibitors in initial screens can be further tested to evaluate the mechanism whereby these agents/molecules block MMP-2/TLR-2 binding. TLR-2-expressing cells, such as those described herein, can be incubated with agents/molecules and molecular interactions assessed using methods, such as, e.g., co-immunoprecipitation of MMP-2 and TLR-2 from the cell lysates. A difference in MMP-2/TLR2 binding in the presence of the agent/molecule relative to that of a control agent/molecule would indicate whether or not the interaction is direct. Additional methods can be used to evaluate if MMP-2 and TLR-2 interact directly, including other affinity-based methods (e.g., affinity chromatography or panning), competitive inhibition assays, and various visualization techniques, such as fluorescence resonance energy transfer (FRET) and others which are known in the art. Further to this point, FIG. 8 presents results that strongly suggest that MMP-2 and TLR-2 interact directly.

HEK-blue/TLR technology (InvivoGen) was used to determine whether MMP-2 signals through TLRs. HEK 293 engineered cell lines transfected with individual hTLRs and expressing an NF-κB-inducible SEAP (secreted embryonic alkaline phosphatase) reporter gene were incubated overnight with MMP-2. NF-κB activation was assessed by addition of the SEAP detection media Quanti-Blue (Invivogen).

Agents identified using the screening assays described herein can be used in therapeutic applications directed to promoting $T_H1$ responses to MMP-2 expressing tumors and, more particularly, to promoting MMP-2 specific $T_H1$ responses to MMP-2 expressing tumors so as to induce a more effective immune response against MMP-2 expressing tumors in patients in need thereof. Methods described herein are further directed to using such agents to modulate the MMP-2 directed $T_H2$ promoting microenvironment so as to create a microenvironment that promotes differentiation and activation of MMP-2 specific $T_H1$ cells, as reflected in the number of MMP-2 specific $T_H1$ cells induced therein.

Enzymatically inactive MMP-2 (SEQ ID NO: 1) may, moreover, be useful in screening assays described herein as, for example, a positive control against which the activity of potential inhibitor molecules may be screened. Enzymatically inactive MMP-2 may be produced by treating isolated MMP-2 using heat inactivation or contact with MMP-2 specific inhibitors as described below or potentially by treatment with chemical inactivators or irradiation. Nucleic acid sequences encoding enzymatically inactive MMP-2 and sub-fragments thereof are also envisioned as useful in, for example, screening assays described herein. Such nucleic acid sequences would encode an enzymatically dead or inactive variant of MMP-2 or sub-fragment thereof and thus, would include mutations within the context of the nucleic acid sequence encoding MMP-2 (SEQ ID NO: 13) or sub-fragment thereof. The catalytic domain of MMP-2 is, for example, known in the art and mutations that alter critical residues encoded thereby are envisioned for this purpose. A homozygous 1210G-A transition in exon 8 of the MMP2 gene, leads to glu-to-lys (E404K) substitution in the catalytic domain of the protein. The glutamic acid at codon 404 is believed to be essential for the peptidase activity of all metalloproteinases, as its carboxyl group catalyzes 2 proton transfers, helps stabilize the transition state, and triggers the release of the products. Additional inactivating mutations are also envisioned, such as a G-to-A transition in codon 101 of exon 2 of MMP2, which is known to result in replacement of an arginine by histidine (R101H) in the prodomain, a region highly conserved across species and other members of the MMP gene family that is involved in autoproteolytic activation of MMP2. See also Brooks et al. (Cell 92:391, 1998), the entire contents of which is incorporated herein by reference in its entirety, and references cited therein.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R1. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A. Terminology

The term "specific binding member" describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organization of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. This application is concerned in part with antigen-antibody type reactions.

The term "antibody" describes an immunoglobulin whether natural or partly or wholly synthetically produced. The term also covers any polypeptide or protein having a binding domain which is, or is homologous to, an antibody binding domain. CDR grafted antibodies are also contemplated by this term. An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. The term "antibody(ies)" includes a wild type immunoglobulin (Ig) molecule, generally comprising four full length polypeptide chains, two heavy (H) chains and two light (L) chains, or an equivalent Ig homologue thereof (e.g., a camelid nanobody, which comprises only a heavy chain); including full length functional mutants, variants, or derivatives thereof, which retain the essential epitope binding features of an Ig molecule, and including dual specific, bispecific, multispecific, and dual variable domain antibodies; Immunoglobulin molecules can be of any class (e.g., IgG, IgE, IgM, IgD, IgA, and IgY), or subclass (e.g., IgG1, IgG2, IgG3, IgG4, IgA1, and IgA2). Also included within the meaning of the term "antibody" is any "antibody fragment".

An "antibody fragment" means a molecule comprising at least one polypeptide chain that is not full length, including (i) a Fab fragment, which is a monovalent fragment consisting of the variable light (VL), variable heavy (VH), constant light (CL) and constant heavy 1 (CH1) domains; (ii) a F(ab')2 fragment, which is a bivalent fragment comprising two Fab fragments linked by a disulfide bridge at the hinge region; (iii) a heavy chain portion of an Fab (Fd)

fragment, which consists of the VH and CH1 domains; (iv) a variable fragment (Fv) fragment, which consists of the VL and VH domains of a single arm of an antibody, (v) a domain antibody (dAb) fragment, which comprises a single variable domain (Ward, E. S. et al., Nature 341, 544-546 (1989)); (vi) a camelid antibody; (vii) an isolated complementarity determining region (CDR); (viii) a Single Chain Fv Fragment wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (ix) a diabody, which is a bivalent, bispecific antibody in which VH and VL domains are expressed on a single polypeptide chain, but using a linker that is too short to allow for pairing between the two domains on the same chain, thereby forcing the domains to pair with the complementarity domains of another chain and creating two antigen binding sites (WO94/13804; P. Holliger et al Proc. Natl. Acad. Sci. USA 90 6444-6448, (1993)); and (x) a linear antibody, which comprises a pair of tandem Fv segments (VH-CH1-VH-CH1) which, together with complementarity light chain polypeptides, form a pair of antigen binding regions; (xi) multivalent antibody fragments (scFv dimers, trimers and/or tetramers (Power and Hudson, J. Immunol. Methods 242: 193-204 9 (2000)); and (xii) other non-full length portions of heavy and/or light chains, or mutants, variants, or derivatives thereof, alone or in any combination.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023 and U.S. Pat. Nos. 4,816,397 and 4,816,567.

An "antibody combining site" is that structural portion of an antibody molecule comprised of light chain or heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contain the paratope, including those portions known in the art as Fab, Fab', F(ab')$_2$ and F(v), which portions are preferred for use in the therapeutic methods described herein.

Antibodies may also be bispecific, wherein one binding domain of the antibody is a specific binding member of the invention, and the other binding domain has a different specificity, e.g. to recruit an effector function or the like. Bispecific antibodies of the present invention include wherein one binding domain of the antibody is a specific binding member of the present invention, including a fragment thereof, and the other binding domain is a distinct antibody or fragment thereof, including that of a distinct anti-cancer or anti-tumor specific antibody. The other binding domain may be an antibody that recognizes or targets a particular cell type, as in a neural or glial cell-specific antibody. In the bispecific antibodies of the present invention the one binding domain of the antibody of the invention may be combined with other binding domains or molecules which recognize particular cell receptors and/or modulate cells in a particular fashion, as for instance an immune modulator (e.g., interleukin(s)), a growth modulator or cytokine (e.g. tumor necrosis factor (TNF) or a toxin (e.g., ricin) or anti-mitotic or apoptotic agent or factor.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may also contain an antibody molecule having a plurality of antibody combining sites, each immunospecific for a different antigen; e.g., a bispecific (chimeric) monoclonal antibody.

The term "antigen binding domain" describes the part of an antibody which comprises the area which specifically binds to and is complementary to part or all of an antigen. Where an antigen is large, an antibody may bind to a particular part of the antigen only, which part is termed an epitope. An antigen binding domain may be provided by one or more antibody variable domains. Preferably, an antigen binding domain comprises an antibody light chain variable region (VL) and an antibody heavy chain variable region (VH).

The term "specific" may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

The term "adjuvant" refers to a compound or mixture that enhances the immune response, particularly to an antigen. An adjuvant can serve as a tissue depot that slowly releases the antigen and also as a lymphoid system activator that non-specifically enhances the immune response (Hood et al., *Immunology, Second Ed.,* 1984, Benjamin/Cummings: Menlo Park, Calif., p. 384). Often, a primary challenge with an antigen alone, in the absence of an adjuvant, will fail to elicit a humoral or cellular immune response. Previously known and utilized adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvant such as BCG (bacille Calmette-Guerin) and *Corynebacterium parvum*. Mineral salt adjuvants include but are not limited to: aluminum hydroxide, aluminum phosphate, calcium phosphate, zinc hydroxide and calcium hydroxide. Preferably, the adjuvant composition further comprises a lipid of fat emulsion comprising about 10% (by weight) vegetable oil and about 1-2% (by weight) phospholipids. Preferably, the adjuvant composition further optionally comprises an emulsion form having oily particles dispersed in a continuous aqueous phase, having an emulsion forming polyol in an amount of from about 0.2% (by weight) to about 49% (by weight), optionally a metabolizable oil in an emulsion-forming amount of up to 15% (by weight), and optionally a glycol ether-based surfactant in an emulsion-stabilizing amount of up to about 5% (by weight).

As used herein, the term "immunomodulator" refers to an agent which is able to modulate an immune response. An example of such modulation is an enhancement of cell activation or of antibody production.

The term "effective amount" of an immunomodulator refers to an amount of an immunomodulator sufficient to enhance a vaccine-induced immune response, be it cell-mediated, humoral or antibody-mediated. An effective amount of an immunomodulator, if injected, can be in the range of about 0.1-1,000 µg, preferably 1-900 µg, more preferably 5-500 µg, for a human subject, or in the range of about 0.01-10.0 µg/Kg body weight of the subject animal. This amount may vary to some degree depending on the mode of administration, but will be in the same general range. If more than one immunomodulator is used, each one may be present in these amounts or the total amount may fall within this range. An effective amount of an antigen may be an amount capable of eliciting a demonstrable immune response in the absence of an immunomodulator. For many antigens, this is in the range of about 5-100 µg for a human subject. The appropriate amount of antigen to be used is dependent on the specific antigen and is well known in the art.

The exact effective amount necessary will vary from subject to subject, depending on the species, age and general condition of the subject, the severity of the condition being treated, the mode of administration, etc. Thus, it is not possible to specify an exact effective amount. However, the appropriate effective amount may be determined by one of ordinary skill in the art using only routine experimentation or prior knowledge in the vaccine art.

An "immunological response" to a composition or vaccine comprised of an antigen is the development in the host of a cellular- and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

The term "comprise" is generally used in the sense of include, that is to say permitting the presence of one or more features or components.

The term "consisting essentially of" refers to a product, particularly a peptide sequence, of a defined number of residues which is not covalently attached to a larger product. In the case of the peptide of the invention referred to above, those of skill in the art will appreciate that minor modifications to the N- or C-terminal of the peptide may however be contemplated, such as the chemical modification of the terminal to add a protecting group or the like, e.g. the amidation of the C-terminus.

The term "isolated" refers to the state in which specific binding members of the invention, or nucleic acid encoding such binding members will be, in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtiter plates for use in immunoassays, or will be mixed with pharmaceutically acceptable carriers or diluents when used in diagnosis or therapy.

As used herein, "pg" means picogram, "ng" means nanogram, "ug" or "µg" mean microgram, "mg" means milligram, "ul" or "µl" mean microliter, "ml" means milliliter, "l" means liter.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding MMP-2 or peptide sequences therein (such as any one of SEQ ID NOs: 2-12) or comprising or consisting of sequences which are degenerate thereto. DNA sequences having the nucleic acid sequence encoding the peptides of the invention are contemplated, including degenerate sequences thereof encoding the same, or a conserved or substantially similar, amino acid sequence. By "degenerate to" is meant that a different three-letter codon is used to specify a particular amino acid. It is well known in the art that the following codons can be used interchangeably to code for each specific amino acid:

Phenylalanine (Phe or F)
UUU or UUC

Leucine (Leu or L)
UUA or UUG or CUU or CUC or CUA or CUG

Isoleucine (Ile or I)
AUU or AUC or AUA

Methionine (Met or M)
AUG

Valine (Val or V)
GUU or GUC of GUA or GUG

Serine (Ser or S)
UCU or UCC or UCA or UCG or AGU or AGC

Proline (Pro or P)
CCU or CCC or CCA or CCG

Threonine (Thr or T)
ACU or ACC or ACA or ACG

Alanine (Ala or A)
GCU or GCC or GCA or GCG

Tyrosine (Tyr or Y)
UAU or UAC

Histidine (His or H)
CAU or CAC

Glutamine (Gln or Q)
CAA or CAG

Asparagine (Asn or N)
AAU or AAC

Lysine (Lys or K)
AAA or AAG

Aspartic Acid (Asp or D)
GAU or GAC

Glutamic Acid (Glu or E)
GAA or GAG

Cysteine (Cys or C)
UGU or UGC

Arginine (Arg or R)
CGU or CGC or CGA or CGG or AGA or AGG

Glycine (Gly or G)
GGU or GGC or GGA or GGG

Tryptophan (Trp or W)
UGG

Termination codon
UAA (ochre) or UAG (amber) or UGA (opal)

It should be understood that the codons specified above are for RNA sequences. The corresponding codons for DNA have a T substituted for U.

Mutations can be made in the sequences encoding the protein or peptide sequences of the MMP-2 proteins, peptides or immune activator proteins or peptides of the invention, such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:
Amino Acids with Nonpolar R Groups
Alanine, Valine, Leucine, Isoleucine, Proline, Phenylalanine, Tryptophan, Methionine
Amino Acids with Uncharged Polar R Groups
Glycine, Serine, Threonine, Cysteine, Tyrosine, Asparagine, Glutamine
Amino Acids with Charged Polar R Groups (Negatively Charged at pH 6.0)
Aspartic acid, Glutamic acid
Basic Amino Acids (Positively Charged at pH 6.0)
Lysine, Arginine, Histidine (at pH 6.0)

Another grouping may be those amino acids with phenyl groups:
Phenylalanine, Tryptophan, Tyrosine Another grouping may be according to molecular weight (i.e., size of R groups):

| Glycine | 75 | Alanine | 89 |
| --- | --- | --- | --- |
| Serine | 105 | Proline | 115 |
| Valine | 117 | Threonine | 119 |
| Cysteine | 121 | Leucine | 131 |
| Isoleucine | 131 | Asparagine | 132 |
| Aspartic acid | 133 | Glutamine | 146 |
| Lysine | 146 | Glutamic acid | 147 |
| Methionine | 149 | Histidine (at pH 6.0) | 155 |
| Phenylalanine | 165 | Arginine | 174 |
| Tyrosine | 181 | Tryptophan | 204 |

Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free NH$_2$ can be maintained.

Exemplary and preferred conservative amino acid substitutions include any of: glutamine (Q) for glutamic acid (E) and vice versa; leucine (L) for valine (V) and vice versa; serine (S) for threonine (T) and vice versa; isoleucine (I) for valine (V) and vice versa; lysine (K) for glutamine (Q) and vice versa; isoleucine (I) for methionine (M) and vice versa; serine (S) for asparagine (N) and vice versa; leucine (L) for methionine (M) and vice versa; lysine (L) for glutamic acid (E) and vice versa; alanine (A) for serine (S) and vice versa; tyrosine (Y) for phenylalanine (F) and vice versa; glutamic acid (E) for aspartic acid (D) and vice versa; leucine (L) for isoleucine (I) and vice versa; lysine (K) for arginine (R) and vice versa.

Amino acid substitutions may also be introduced to substitute an amino acid with a particularly preferable property. For example, a Cys may be introduced a potential site for disulfide bridges with another Cys. A H is may be introduced as a particularly "catalytic" site (i.e., H is can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues, preferably at least about 80%, and most preferably at least about 90, 91, 92, 93, 94, 95, 96, 97, 98, or 99% of the amino acid residues are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

The term 'agent' means any molecule, including MMP-2-derived peptides or other polypeptides, antibodies, polynucleotides, chemical compounds and small molecules. In particular the term agent includes compounds such as test compounds or drug candidate compounds. The term 'modulator agent" as used herein refers to an agent whose presence alters an interaction (e.g., a biochemical or physical interaction) relative to a control or inert agent. A modulator agent may, therefore, increase/enhance or decrease/reduce such an interaction relative to a control or inert agent. In a particular aspect, a modulator agent identified in a screening assay described herein inhibits MMP-2/TLR2 interactions and is, therefore, identified as an inhibitor.

The term 'agonist' refers to a ligand that stimulates the receptor to which the ligand binds in the broadest sense or stimulates a response that would be elicited on binding of a natural ligand to a binding site.

The term 'assay' means any process used to measure a specific property of a compound or agent. A 'screening assay' means a process used to characterize or select compounds based upon their activity from a collection of compounds.

"Preventing" or "prevention" refers to a reduction in risk of acquiring a disease or disorder.

The term 'prophylaxis' is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

The term 'treating' or 'treatment' of any disease or infection refers, in one embodiment, to ameliorating the disease or infection (i.e., arresting the disease or growth of the infectious agent or bacteria or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or infection, either physically, (e.g., stabilization of a discernible symptom), physiologically, (e.g., stabilization of a physical parameter), or both. In a further embodiment, 'treating' or 'treatment' relates to slowing the progression of a disease.

The phrase "pharmaceutically acceptable" refers to molecular entities and compositions that are physiologically tolerable and do not typically produce an allergic or similar untoward reaction, such as gastric upset, dizziness and the like, when administered to a human.

As used herein, the term "autologous" refers to organs, tissues, cells, or proteins isolated from a donor patient that are later re-introduced into the donor patient. Accordingly, the donor and recipient are the same patient in autologous transfers. The term "autologous T cells", for example, refers to T cells that have been isolated from a subject and then administered to the same patient. Typically, and in accordance with the present methods, the isolated T cells may be stimulated in cell culture prior to administration to the patient.

B. Further Aspects of the Detailed Description

The invention relates generally to methods and agents for inducing immune responses to tumors that express MMP-2. Prior to the discoveries detailed herein, there was no appreciation that MMP-2 and tumors expressing MMP-2 (e.g., melanoma) influence the cellular microenvironment so as to promote differentiation/induction of inflammatory $T_H2$ cells at the expense of more effective $T_H1$ cell-based responses and this adverse influence is mediated, at least in part, by MMP-2 mediated activation of TLR2, which in turn leads to upregulation of OX40L on dendritic cells. This insight into the mechanism/s whereby tumors expressing MMP-2 subvert the immune response to be a less effective weapon against tumor cell clearance has been used to advantage to design new screening assays and methods for using same to identify agents that modulate MMP-2/TLR2 interaction, agents identified thereby and therapeutic regimens utilizing these agents. Also subsumed herein are novel MMP-2 sub-fragments that may be used to advantage for therapeutic purposes. Such MMP-2 sub-fragments may span 4-50-mer contiguous amino acids of SEQ ID NO: 1 or, for example, the first two-thirds of SEQ ID NO: 1.

Accordingly, methods and agents for inducing an effective immune response to tumors that express MMP-2, including melanoma, are presented herein. In one aspect, a method directed to promoting $T_H1$ responses to MMP-2 expressing tumors and, more particularly, to promoting MMP-2 specific $T_H1$ responses to MMP-2 expressing tumors so as to induce a more effective immune response against the MMP-2 expressing tumors is presented. Methods described herein are further directed to modulating the MMP-2 driven $T_H2$ promoting microenvironment so as to create a microenvironment that promotes differentiation and activation of MMP-2 specific $T_H1$ cells, as reflected in a decrease in OX40L expression and a decrease in NF-κB activation in dendritic cells in the tumor microenvironment; decreased expression of inflammatory cytokines, such as IL-1β, IL-6, IL-8, and TNFα; an increase in the number of MMP-2 specific $T_H1$ cells induced thereby and/or increased levels of cytokines that are characteristic of $T_H1$ cells, such as IFNγ and IL-2. A decrease in the number of $T_H2$ cells and/or decreased levels of cytokines characteristic of $T_H2$ cells, such as IL-4 and IL-13, may also be used as an indicator of effective modulation of the tumor microenvironment to achieve a microenvironment that promotes differentiation and activation of MMP-2 specific $T_H1$ cells.

In that MMP-2-conditioned DCs prime $T_H2$ directed responses against several other MAAs (in addition to MMP-2), the present method is also directed to promoting MMA specific $T_H1$ responses to melanoma cells so as to induce a more effective immune response against melanomas. Methods described herein are further directed to modulating the MMP-2 driven $T_H2$ promoting microenvironment so as to create a microenvironment that promotes differentiation and activation of MMA specific $T_H1$ cells, as reflected in a decrease in OX40L expression and a decrease in NF-κB activation in dendritic cells in the tumor microenvironment; decreased expression of inflammatory cytokines, such as IL-1β, IL-6, IL-8, and TNFα; an increase in the number of MMA specific $T_H1$ cells induced thereby and/or increased levels of cytokines that are characteristic of $T_H1$ cells, such as IFNγ and IL-2. A decrease in the number of $T_H2$ cells, and/or decreased levels of cytokines characteristic of $T_H2$ cells, such as IL-4 and IL-13, and/or decreased levels of CD4$^+$ T cells expressing GATA-3 may also be used as indicators of effective modulation of the tumor microenvironment to achieve a microenvironment that promotes differentiation and activation of $T_H1$ cells specific for MMAs in general, including MMP-2.

The present invention provides assays for screening and identifying agents, compounds or peptides to modulate immune response to an MMP-2 expressing tumor (e.g., a melanoma), indicators to evaluate the effectiveness of an immune response to an MMP-2 expressing tumor (e.g., a melanoma), and methods for stimulating or facilitating immune response to an MMP-2 expressing tumor (e.g., a melanoma). The methods, assays, and indicators described herein are based, in part, on the ability of MMP-2-conditioned DCs to up-regulate OX40L expression and to the novel discovery that MMP-2 acts via interaction with TLR2 on dendritic cells (DCs) to activate NF-κB signaling, which in turn leads to increased expression of OX40L on DCs. The methods, agents and assays of the invention can be implemented in therapeutic strategies (e.g., vaccine strategies) directed to the stimulation of a $T_H1$ cell-based immune response to an MMP-2 expressing tumor, such as melanoma.

Thus, a purpose of the present method is to induce an effective immune response to MMP-2 expressing tumors, including melanoma. As described above, triggering an effective $T_H1$ cell-based immune response to MMP-2 expressing tumors comprises one aspect of an effective immune response. The methods, assays, and indicators described herein are also envisioned as useful in triggering an effective antibody-based response to MMP-2 and tumors expressing same. This invention thus provides a means to overcome earlier failures to develop MMP-2 based pharmaceutical and immunogenic compositions and vaccines.

MMP-2 sub-fragments that comprise a CD4$^+$ T cell epitope and/or possess the ability to modulate (e.g., inhibit) MMP-2/TLR2 interaction on DCs are also envisioned as potential immunogens because they may elicit antibodies that act as inhibitory antibodies capable of blocking MMP-2 mediated activation of TLR2 on DCs. The relative positions within full length MMP-2 and amino acid sequences of the 11 MMP-2-derived peptides identified as specific epitopes recognized by CD4$^+$ T cell clones are as follows: P1-20: MEALMARGALTGPLRALCLL (SEQ ID NO: 2); P11-30: TGPLRALCLLGCLLSHAAAA (SEQ ID NO: 3); P21-40: GCLLSHAAAAPSPIIKFPGD (SEQ ID NO: 4); P41-60: VAPKTDKELAVQYLNTFYGC (SEQ ID NO: 5); P161-180: RIHDGEADIMINFGRWEHGD (SEQ ID NO: 6); P361-380: ESCTSAGRSDGKMWCATTAN (SEQ ID NO: 7); P551-570: GYPKPLTSLGLPPDVQRVDA (SEQ ID NO: 8); P571-590: AFNWSKNKKTYIFAGDKFWR (SEQ ID NO: 9); P601-620: GFPKLIADAWNAIPDNLDAV (SEQ ID NO: 10); P621-640: VDLQGGGHSYFFK-GAYYLKL (SEQ ID NO: 11); and P631-650: FFK-GAYYLKLENQSLKSVKF (SEQ ID NO: 12). MMP-2 sub-fragments that possess the ability to modulate (e.g., inhibit) MMP-2/TLR2 interaction on DCs may comprise or consist of at least two of the MMP-2 20-mers described herein, including those defined as specific epitopes recognized by CD4$^+$ T cell clones. The MMP-2 sub-fragments or peptides may be combined with, associated with, covalently attached to or fused to other immune modulators, including interferons, interleukins, T or B cell antigens or stimulators, other activators, or adjuvant molecules.

Accordingly, MMP-2 proteins and peptides are described herein which have application and use, alone or in combination with other immune system modulators, T cell modulators, antibodies, vaccines, antigens, or chemotherapeutics for stimulating, facilitating or enhancing desired immune system or immune cell actions or activities, particularly those directed against MMP-2 expressing tumors, that result in tumor regression and/or improved patient survival.

In a further embodiment, the present invention relates to certain therapeutic methods which would be based upon the activity of at least one of an enzymatically inactive sub-fragment of SEQ ID NO: 1 (e.g., the amino terminal two-thirds of SEQ ID NO: 1), or upon agents or other drugs determined to possess the same activity. A therapeutic method is associated with the modulation of the immune response, particularly stimulation or enhancement of immunity and response to MMP-2 expressing tumors, particularly to melanoma. A further therapeutic method is associated with methods for stimulating immune response to MMP-2 expressing tumors comprising administering at least one of an enzymatically inactive sub-fragment of SEQ ID NO: 1, or agents or other drugs determined to possess the same activity, alone or in combination with other MMAs, or other immune modulators, including adjuvants, for generating an immunogenic and/or protective response to MMP-2 expressing tumors. In one aspect of this method, at least one of an enzymatically inactive sub-fragment of SEQ ID NO: 1, or agents or other drugs determined to possess the same activity, are administered to individuals diagnosed as having an MMP-2 expressing tumor, such as melanoma, to stimulate effective immune response to these tumors and clearance of tumor cells.

MMP-2 expressing tumors are known in the art and include the following: melanoma, wherein higher levels of expression are noted in malignant tumors as compared to pre-malignant lesions, and higher levels are correlated with distant metastases and reduced survival; breast cancer, wherein higher levels of expression are noted in malignant tumors as compared to normal tissue, higher activation in malignant tumors is noted as compared to normal tissue, higher levels are correlated with tumor stage, lymph node metastases and distant metastases, and increased levels are correlated with reduced survival; colon cancer, wherein higher levels of expression are noted in malignant tumors as compared to normal tissue, higher activation in malignant tumors is noted as compared to normal tissue, and higher levels are correlated with tumor stage, angiogenesis and local invasion; gastric cancer, wherein higher levels of expression are noted in malignant tumors as compared to normal tissue, higher activation in malignant tumors is noted as compared to normal tissue, and increased levels are correlated with increased invasion and reduced survival; lung cancer, wherein higher levels of expression are noted in malignant tumors as compared to normal tissue, higher activation in malignant tumors is noted as compared to normal tissue, and higher levels are correlated with tumor stage, lymph node metastases and distant metastases; ovarian cancer, wherein higher levels of expression are noted in malignant tumors as compared to pre-malignant lesions, higher activation in malignant tumors is noted as compared to normal tissue, and higher levels are correlated with reduced survival; pancreatic cancer, wherein higher levels of expression are noted in malignant tumors as compared to normal tissue, and higher levels are correlated with lymph node metastases, distant metastases, and reduced survival; prostate cancer, wherein higher levels of expression are noted in malignant tumors as compared to pre-malignant lesions and higher levels are correlated with tumor grade; and squamous cell carcinoma of the head and neck, wherein higher levels of expression are noted in malignant tumors as compared to normal tissue, and higher levels are correlated with lymph node metastases, distant metastases, reduced survival, and poor treatment response. See Egeblad M and Werb Z, New functions for the matrix metalloproteinases in cancer progression. Nat Rev Cancer. 2002 March; 2(3):161-74, the entire content of which is incorporated herein by reference.

The present invention also includes enzymatically inactive SEQ ID NO: 1 or a fragment thereof, or agents or other drugs determined to possess the same activity, which are covalently attached to or otherwise associated with other molecules or agents. These other molecules or agents include, but are not limited to, molecules (including antibodies or antibody fragments) with distinct recognition, targeting or binding characteristics, immune cell modulators, immune cell antigens, toxins, ligands, adjuvants, and chemotherapeutic agents.

Peptides and proteins of the invention may be labelled with a detectable or functional label. Detectable labels include, but are not limited to, radiolabels such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{121}I$, $^{124}I$, $^{125}I$, $^{131}I$, $^{111}In$, $^{117}Lu$, $^{211}At$, $^{198}Au$, $^{67}Cu$, $^{225}Ac$, $^{213}Bi$, $^{99}Tc$ and $^{186}Re$, which may be attached to antibodies of the invention using conventional chemistry known in the art of antibody imaging. Labels also include fluorescent labels (for example fluorescein, rhodamine, Texas Red) and labels used conventionally in the art for MRI-CT imaging. They also include enzyme labels such as horseradish peroxidase, (β-glucoronidase, β-galactosidase, and urease. Labels further include chemical moieties such as biotin which may be detected via binding to a specific cognate detectable moiety, e.g. labelled avidin. Functional labels include substances which are designed to be targeted to the site of a tumor to cause destruction of tumor tissue. Such functional labels include cytotoxic drugs such as 5-fluorouracil or ricin and enzymes such as bacterial carboxypeptidase or nitroreductase, which are capable of converting prodrugs into active drugs at the site of a tumor.

Peptides of and of use in the present invention may include synthetic, recombinant or peptidomimetic entitites. The peptides may be monomers, polymers, multimers, dendrimers, concatamers of various forms known or contemplated in the art, and may be so modified or mutlimerized so as to improve activity, specificity or stability. For instance, and not by way of limitation, several strategies have been pursued in efforts to increase the effectiveness of antimicrobial peptides including dendrimers and altered amino acids (Tam et al (2002) Eur J Biochem 269 (3): 923-932; Janiszewska et al (2003) Bioorg Med Chem Lett 13 (21):3711-3713; Ghadiri et al. (2004) Nature 369(6478):301-304; DeGrado et al (2003) Protein Science 12(4):647-665; Tew et al. (2002) PNAS 99(8):5110-5114; Janiszewska et al (2003) Bioorg Med Chem Lett 13 (21): 3711-3713). U.S. Pat. No. 5,229,490 discloses a particular polymeric construction formed by the binding of multiple antigens to a dendritic core or backbone.

Protamines or polycationic amino acid peptides containing combinations of one or more recurring units of cationic amino acids, such as arginine (R), tryptophan (W), lysine (K), even synthetic polyarginine, polytryptophan, polylysine, have been shown to be capable of killing microbial cells. These peptides cross the plasma membrane to facilitate uptake of various biopolymers or small molecules (Mitchell D J et al (2002) J Peptide Res 56(5):318-325).

Conjugates or fusion proteins of the present invention, wherein enzymatically inactive fragments of SEQ ID NO: 1 as described herein are conjugated or attached to other molecules or agents further include, but are not limited to binding members conjugated to a cell targeting agent or sequence, chemical ablation agent, toxin, immunomodulator, cytokine, cytotoxic agent, chemotherapeutic agent or drug.

Uptake and targeting of DCs can be achieved using a variety techniques known in the art, including coupling to antibodies targeting DC-specific surface molecules (Romani et al., 2010; the entire contents of which is incorporated herein in its entirety, including references cited therein); utilization of engineered Sindbis envelope that specifically target DC instead of VSV-G (Yang et al., 2008; the entire content of which is incorporated herein in its entirety); site of administration; blood infusion; or ex vivo culture of DC, treatment of ex vivo cultured DC to introduce the desired construct/s, and re-injection of same into subject in need thereof.

In vitro assays are described herein which may be utilized by the skilled artisan to further or additionally screen, assess, and/or verify the activities of enzymatically inactive fragments of SEQ ID NO: 1 as described herein, including further assessing immune response targeted against MMP-2 expressing tumor cells. Cell based assays and in vitro methods are described herein and were utilized to perform experiments as described, for example, in the Examples.

In vivo animal models of human MMP-2 expressing tumors and melanoma or immune response to same may be utilized by the skilled artisan to further or additionally screen, assess, and/or verify the activity of enzymatically inactive fragments of SEQ ID NO: 1 as described herein, including further assessing immune response targeted against MMP-2 expressing tumor cells in vivo. Such animal models include, but are not limited to models of immune system modulation or immune response.

Proteins, peptides, immune activators or agents of the present invention may be administered to a patient in need of treatment via any suitable route, including by intravenous, intraperitoneal, intramuscular injection, or orally. The precise dose will depend upon a number of factors, including whether the proteins, peptides, immune activators or agents are for diagnosis or for treatment or for prevention. The dosage or dosing regime of an adult patient may be proportionally adjusted for children and infants, and also adjusted for other administration or other formats, in proportion for example to molecular weight or immune response. Administration or treatments may be repeated at appropriate intervals, at the discretion of the physician.

Proteins, peptides, immune activators or agents described herein are generally administered in the form of a pharmaceutical composition, which may comprise at least one component in addition to the proteins, peptides, immune activators or agents. Pharmaceutical compositions according to the present invention, and for use in accordance with the present invention, may comprise, in addition to active ingredient, a pharmaceutically acceptable excipient, carrier, buffer, stabiliser or other materials known to those skilled in the art. Such materials should be non-toxic and should not interfere with the efficacy of the active ingredient. The precise nature of the carrier or other material will depend on the route of administration, which may be oral, or by injection, e.g. intravenous, or by deposition at a tumor site.

The mode of administration of an immunogenic composition of the invention, whether of the MMP-2 peptide alone or as part of an immunogenic conjugate, may be by any suitable route which delivers an immunoprotective amount of the protein to the subject. One such route is the parenteral route, such as by intramuscular or subcutaneous administration. Other modes of administration may also be employed, where desired, such as the mucosal route, such as by oral, rectal, buccal or intranasal administration, or via other parenteral routes, i.e., intradermally, intravenously, intraperitoneally, or intratumorally.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient may be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

A composition may be administered alone or in combination with other treatments, therapeutics or agents, either simultaneously or sequentially dependent upon the condition to be treated. In addition, the present invention contemplates and includes compositions comprising the proteins, peptides, immune activators or agents herein described and other agents or therapeutics such as immune modulators, antibodies, immune cell stimulators, or adjuvants. In addition, the composition may be administered with hormones, such as dexamethasone, immune modulators, such as interleukins, tumor necrosis factor (TNF) or other growth factors, colony stimulating factors, or cytokines which stimulate the immune response and reduction or elimination of virus. The composition may also be administered with, or may include combinations along with immune cell antigen antibodies or immune cell modulators.

The preparation of therapeutic compositions which contain polypeptides, analogs or active fragments as active ingredients is well understood in the art. Typically, such compositions are prepared as injectables, either as liquid solutions or suspensions. However, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A protein, peptide, immune activator or agent can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Accordingly, also encompassed herein is a composition comprising at least one of an enzymatically inactive fragment of SEQ ID NO: 1 as described herein or nucleic acid sequences encoding same or an agent identified using a screening assay described herein and a pharmaceutically acceptable buffer, for use in treating a patient with an MMP-2 expressing tumor, such as melanoma, wherein said composition alleviates symptoms of the MMP-2 expressing tumor in the patient when administered to the patient in a therapeutically effective amount. Such compositions may also have utility for use in prophylaxis for a patient at risk for developing an MMP-2 expressing tumor, including melanoma, wherein said composition prevents or alleviates symptoms in the patient when administered to the patient in an effective amount. Also encompassed herein is the use of a therapeutically effective amount of a composition comprising at least one of enzymatically inactive fragment of SEQ ID NO: 1 as described herein or nucleic acid sequences encoding same or an agent identified using a screening assay described herein and a pharmaceutically acceptable buffer in the manufacture of a medicament for treating a patient with an MMP-2 expressing tumor, such as melanoma, wherein the medicament alleviates or prevents symptoms of the MMP-2 expressing tumor when administered to the patient. Also encompassed herein is at least one enzymatically inactive fragment of SEQ ID NO: 1 as described herein or nucleic acid sequences encoding same or an agent identified using a screening assay described herein and compositions thereof for use in treating cancer in a subject.

The peptide or agent containing compositions are conventionally administered intramuscularly, intravenously, as by injection of a unit dose, or orally, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of activation and immune response desired. Precise amounts of active ingredient required to be administered depend on the judgment of the practitioner and are peculiar to each individual. Suitable regimens for initial administration and follow on administration are also variable, and may include an initial administration followed by repeated doses at appropriate intervals by a subsequent injection or other administration.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

In accordance with the present methods, T cells may be isolated from a subject or patient via methods routinely practiced by skilled practitioners. In brief, most approaches call for isolation of a blood sample from the subject and subsequent isolation of peripheral blood lymphocytes (PBLs) therefrom. T cells of different types can then be purified via a variety of means, including fluoresence activated cell sorting (FACS) and affinity purification using cell type specific markers. Peripheral blood mononuclear cells may, for example, be collected from human donors by leukapheresis and further purified on ficoll-sodium metrizoate density gradients, after which such cells are typically washed extensively and may, as necessary, be frozen in a solution of 10% DMSO, 2% human serum albumin in phosphate buffered saline. Protocols for isolating, purifying, and re-introducing T cells to subjects are, moreover, known in the art and described in standard textbooks of clinical immunology and described in references in the literature, including Godet et al. (J Exp Med 205:2673, 2008); Vignard et al. (J immunol 175:4797, 2005); and Khammari et al. (J Invest Derm 129:2835, 2009), the contents of each of which is specifically incorporated herein by reference.

As described herein, lymphocytes can be obtained either from a classical Ficoll of the patient's blood or from tumor fragments (tumor infiltrating lymphocytes, TILs). In the latter case, TILs can be isolated by culturing cryopreserved fragments of melanoma-invaded lymph nodes in 12-well tissue culture plates with X-vivo 15 medium containing 150 IU/ml rhIL-2 and 1 nM glutamine for 10 to 14 days. To perform high-fold expansion, $1.8 \times 10^6$ short-term culture TILs are plated at 300 viable lymphocytes/well with irradiated feeder cells into U-bottomed microplates in 200 nl rhIL-2 medium. Phytohemagglutinin is added on day 0 (15 µg/ml). After 48 h, most of the PHA is removed by replacing the culture medium. Ten days later, lymphocytes are removed from the culture plates, adjusted to $1 \times 10^6$ cells/ml in rIL-2 medium and transferred into culture trays for an additional 10 days before injection.

A brief protocol for isolating T and B cells from peripheral blood excerpted from Protocol Online (contributed by Nance E. Donacki, modified February 2009) is as follows:
Reagents
Heparin-1000 U/ml
Ficoll-Hypaque
PBS
RPMI-1640 supplemented with 10 mM glutamine and 15% FBS
AET (0.14M) Dissolve 1.967 g AET in 35 ml di-H2O.
Adjust to pH 8.0 with 1.0N NaOH. Bring volume to 50 ml with di-H2O.
Store at 2-8° C. Check pH every 2 weeks.
AET-treated SRBC
Wash SRBC 4 times with PBS
Add 4 volumes AET to 1 volume packed SRBC in a 15 m conical tube (1 ml of AET+0.25 ml packed SRBC).
Mix well. Incubate in a 37° C. water bath for 30 minutes. Shake vigorously.
Wash 3 times with PBS.
Store in PBS at 2-8° C. for up to 3 days.
SRBC-Absorbed FBS
Mix 10 volumes of FBS with 1 volume packed SRBC.
Incubate at 37° C. for 30 minutes.
Incubate at 2-8° C. for 30 minutes.
Centrifuge at 400 g for 10 minutes.
Collect the FBS. Filter sterilize. Store aliquots at −20° C.
Preparation of PBL's
Draw peripheral blood into syringe containing 10 U/ml heparin.
Dilute the blood 1:1 with PBS.
Layer 30 ml of diluted blood onto 20 ml Ficoll-Hypaque.
Centrifuge at 1550 rpm for 30 minutes, room temperature.
Aspirate and discard the supernatant.
Carefully collect the interface of PBL's and transfer into a clean tube.
Fill the tube with PBS. Centrifuge at 1550 rpm for 10 minutes.
Wash the pellet 2 times with PBS.
Count the cells and resuspend to $10^7$ cells/ml in PBS.
Separation of T-Cells
Mix 1 ml of AET-treated SRBC with 10 ml FBS.

Mix and equal volume of PBL's with a 1% (v/v) mixture of AET-SRBC FBS in a 50 ml tube.

Incubate in a 37° C. water bath for 10 minutes.

Centrifuge at 200 g for 10 minutes. Make sure that the cells have pelleted. If not, re-centrifuge for 5 minutes.

Place the tube upright on ice for 60 min.

Layer super over 15 ml of Ficoll-Hypaque leaving 7.5 ml of fluid above the pellet.

Resuspend the pellet by rotating the tube along the long axis.

Stand upright for 1 minute. Remove the top 5 ml and layer on Ficoll-Hypaque.

Rotate as above and transfer to gradient tube.

Wash the tube with 5 ml of PBS and add to gradient.

Centrifuge at 300 g for 40 minutes, room temperature.

Collect the B cells at the interface. Wash 3 times with PBS.

Suspend the SRBC-T cell pellet. Centrifuge at 300 d for 10 minutes.

Aspirate all of the supernatant. Break up the cell pellet by gently shaking.

Add 9 ml of di-H2O with shaking for 4 seconds.

Add 1 ml of 10×PBS with shaking.

Immediately fill the tube with 1×PBS.

Centrifuge at 300 g for 10 minutes, and wash 2 times with PBS.

It will be understood that variations in the above protocol are also envisioned and known in the art and the above protocol is presented for illustrative purposes only and is not intended to be limiting.

In accordance with the methods described herein, isolated T cells may be activated in vitro using cell culture systems as described herein or by following routine protocols understood in the art. Activated T cells (e.g., MMP-2 specific $T_H1$ cells) may then be selected based on epitope specificity, functional capacities such as cytokine secretion, proliferative capacity, differentiation status, and/or anti-tumor activity. Activated, selected T cells are then administered to a subject/patient in need thereof using techniques known in the art such as intravenous or intramuscular injection, local injection in the vicinity of an MMP-2 expressing tumor, and/or intratumoral injection.

In accordance with the above, an assay system for screening potential agents/drugs effective to modulate MMP-2 mediated activation of TLR2 responsive to tumor-derived MMP-2 (e.g., melanoma), may be prepared. MMP-2 peptides, for example, may be introduced into a test system, and the prospective agent/drug may also be introduced into the resulting cell culture, and the culture thereafter examined to observe any changes in the activity of the cells, or amount and extent of immune response indicator activity (for example, measuring nuclear factor-κB (NF-κB) signaling, secretion of inflammatory cytokines, or OX40 ligand (OX40L) expression on the cell (e.g., a dendritic cell) due either to the addition of the prospective drug alone, or due to the effect of added quantities of the known peptides and/or agent(s).

Nucleic Acids

The present invention further provides an isolated nucleic acid encoding a protein, peptide, immune activator or agent of the present invention. Nucleic acid includes DNA and RNA. In a preferred aspect, the present invention provides a nucleic acid which codes for a polypeptide of the invention as defined above, including any one of SEQ ID NO: 1 or a fragment thereof as set out herein.

The present invention also provides constructs in the form of plasmids, vectors, and transcription or expression cassettes which comprise at least one polynucleotide as above.

The present invention also provides a recombinant host cell which comprises one or more constructs as above. A nucleic acid encoding any specific binding member as provided herein forms an aspect of the present invention, as does a method of production of the specific binding member which method comprises expression from encoding nucleic acid therefor. Expression may conveniently be achieved by culturing recombinant host cells containing the nucleic acid under appropriate conditions. Following production by expression, a specific binding member may be isolated and/or purified using any suitable technique, then used as appropriate.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is E. coli. The expression of antibodies and antibody fragments in prokaryotic cells such as E. coli is well established in the art.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The disclosures of Sambrook et al. and Ausubel et al. are incorporated herein by reference.

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene. The present invention also provides a method which comprises using a construct as stated above in an expression system in order to express a specific binding member or polypeptide as above.

Another feature of this invention is the expression of DNA sequences contemplated herein, particularly encoding the MMP-2 peptides, immune activator or agent of the invention. As is well known in the art, DNA sequences may be expressed by operatively linking them to an expression control sequence in an appropriate expression vector and employing that expression vector to transform an appropriate unicellular host. A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col El, pCR1, pBR322, pMB9 and their derivatives, plasmids such as RP4; phage DNAs, e.g., the numerous derivatives of phage λ, e.g., NM989, and other phage DNA, e.g., M13 and filamentous single stranded phage DNA; yeast plasmids such as the 2µ, plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences (sequences that control the expression of a DNA sequence operatively linked to it) may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli, Pseudomonas, Bacillus, Streptomyces*, fungi such as yeasts, and animal cells, such as CHO, YB/20, NSO, SP2/0, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products. Considering these and other factors a person skilled in the art will be able to construct a variety of vector/expression control sequence/host combinations that will express the DNA sequences of this invention on fermentation or in large scale animal culture.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

Example 1

Introduction

Matrix metalloproteinase-2 (MMP-2) is a proteolytic enzyme that degrades the extracellular matrix and is overexpressed by many tumors. The present inventors have previously documented the presence of MMP-2-specific CD4$^+$ T cells in tumor-infiltrating lymphocytes (TILs) from melanoma patients, which display an inflammatory $T_H2$ profile, i.e. mainly secreting TNFα, IL-4 and IL-13 and expressing GATA-3. The present inventors, furthermore, demonstrated that MMP-2-conditioned dendritic cells (DCs) prime naive CD4$^+$ T cells to differentiate into an inflammatory $T_H2$ phenotype through OX40L expression and inhibition of IL-12p70 production. Active MMP-2, therefore, acts as a novel endogenous type-2 "conditioner" and may play a role in the observed prevalence of detrimental type-2 responses in melanoma.

As shown herein, the present inventors demonstrate that MMP-2 directed conditioning toward detrimental type-2 responses in MMP-2 expressing tumors (e.g., melanoma) is driven by MMP-2 mediated activation of TLR-2 on dendritic cells. Accordingly, methods to identify modulators of MMP-2 mediated activation of TLR-2 and methods of using same are presented herein as directed to the ongoing desire to identify therapeutic agents (i.e., modulator agents) that may be used for the treatment of MMP-2 expressing tumors such as melanoma. More particularly, methods to identify inhibitors of MMP-2 mediated activation of TLR-2 and methods of using same are presented herein as directed to the ongoing need to identify therapeutic agents (i.e., modulator agents) that may be used for the treatment of MMP-2 expressing tumors such as melanoma.

Experimental Procedures

Reagents.

Purified human MMP-2 (mixture of the proenzyme (50%) and the active form (50%)) can be purchased from Biomol. The MMP-2 enzyme can be inactivated either by heating to 56° C. for 45 min or by addition of the MMP-2 inhibitor III at 100 nM (Calbiochem) for 20 min. rhPEX was purchased from Genway. Overlapping peptides (20 amino acid long overlapping of 10) spanning proMMP-2 sequence were made by Proimmune (>80% pure). Proimmune uses PEPscreen technology, wherein peptides are synthesized on proprietary, state-of-the-art robotic platforms using optimized protocols based on Fmoc-chemistry. In terms of quality control, all peptides are analyzed by MALDI-TOF mass spectrometry to confirm their correct molecular weights. Lyophilized peptides were reconstituted in DMSO and were used either individually (2 µM) or as a pool (204 each). rhGM-CSF was purchased from Immunex. rhIL-4, rhIL-2 were from R&D Systems.

Antibodies.

Antibody to OX40L (11C3.1) was from Biolegend. Blocking antibodies to TLR-2 and TLR-6 were from Invivogen. Antibodies to GATA-3, IL-4 (8D4-8), IL-5 (JES1-39D10), IL-13 (JES10-5A2), TNFα (MAb11), IFNγ (25723.11), perforin (δG9), GranzymeB (GB11), CD40 (5C3), CD80 (L307.4), CD83 (HB15e), CD86 (IT2.2), HLA-DR (TU36), fluorescein isothiocyanate-conjugated antibodies to CD45RA (HI100) and CD45RO (UCHL1), and antibody to CD4 (RPA-T4) were purchased from BD Biosciences Pharmingen. Alexa fluor 488-conjugated antibody to IL-17 (eBio64DEC17), phycoerythrine-conjugated antibody to T-bet (4B10).

T Cell Culture, Stimulation and Priming.

Peripheral blood mononuclear cells (PBMCs) can be purified from healthy donor- (HD) or cord blood donor- (CB) derived buffy coats (New York Blood Center) by Ficoll-Paque Plus (GE Healthcare) centrifugation. $CD4^+$/$CD25^-$ cells were enriched (>90%) by magnetic cell sorting (Miltenyi Biotec) and primed/stimulated for 12-15 days either with irradiated (35Gy) autologous $CD4^-$ cells or with autologous mature DCs in IMDM (GIBCO) supplemented with 1 mM HEPES (Life Technologies), 2 mM L-glutamine (Sigma), streptomycin (100 UI/mL)/penicillin (100 µg/mL) (Sigma) and 5% heat inactivated pooled human serum (PHS; Valley Biomedical) in the presence of rhIL-2 (10 UI/mL) and IL7 (5 ng/mL) (R&D Systems). Antigen presenting cells ($CD4^-$ cells or DCs) were loaded either with peptides (204) or with the MMP-2 protein (10 µg/mL) for 2 and 5 h, respectively. To generate T cell clones, we originally relied on our published methodology (Godefroy et al., 2006; Godefroy et al., 2007; the entire content of each of which is incorporated herein by reference), involving enrichment of IFNγ-secreting cells upon short-term culture and peptide stimulation to generate MMP-2 responsive clones. Briefly, $CD4^+$ T cells were stimulated by $CD4^-$ cells irradiated and pulsed with peptides for 12 days in the presence of rhIL-2 and rhIL-7. $CD4^+$ T cells were then restimulated with peptides for 3 hours before capturing IFNγ-secreting specific cells using a bispecific antibody coating T cells and capturing produced IFNγ. Positive cells were purified magnetically before being cloned. Although MMP-2-specific cells could be isolated, it was realized that IFNγ secretion was marginal compared to their secretion of IL-4 and TNFα. IFNγ-secreting cells in response to MMP-2 peptide pool were enriched by cytokine-guided magnetic cell sorting (Miltenyi Biotec) as described above and cloned the following day by limiting dilution in the presence of irradiated allogeneic PBMCs, 1 µg/mL phytohemagglutinin-L (Sigma) and 150 UI/mL rhIL-2. Tumor infiltrating lymphocytes (TILs) were provided by Pr. F. Jotereau and B. Dréno. They were obtained from tumor-invaded lymph nodes of melanoma patients (stage IIIb) and expanded ex vivo. These patients received autologous TILs and IL-2 infusions in a clinical trial (Labarriere et al., 2002). This protocol was approved by the Institutional Ethics Committee and registered with regulatory state authority in France (Nantes).

Lymphocytes can be obtained either from a classical Ficoll of the patient's blood or from tumor fragments (tumor infiltrating lymphocytes, TILs). In the latter case, TILs can be isolated by culturing cryopreserved fragments of melanoma-invaded lymph nodes in 12-well tissue culture plates with X-vivo 15 medium containing 150 IU/ml rhIL-2 and 1 nM glutamine for 10 to 14 days. To perform high-fold expansion, $1.8 \times 10^6$ of short-term culture TIL were plated at 300 viable lymphocytes/well with irradiated feeder cells into U-bottomed microplates in 200 µl rhIL-2 medium. Phytohemagglutinin was added on day 0 (1 ng/ml). After 48 h, most of the PHA was removed by replacing the culture medium. Ten days later, lymphocytes were removed from the culture plates, adjusted to $1 \times 10^6$ cells/ml in rIL-2 medium and transferred into culture trays for an additional 10 days before injection.

Dendritic Cell Preparation and Activation.

PBMCs were purified from healthy-(HD) or cord blood-(CB) donors and plated at $40 \times 10^6$ cells/10 mL/dish in complete IMDM with 5% PHS. Cells were allowed to adhere for 2 h at 37° C. Non-adherent cells were removed. The monocyte-enriched fraction was supplemented with 100 UI/mL rhGMCSF and 300 UI/mL rhIL-4 (R&D Systems) on days 0, 2 and 4. Immature DCs were harvested on day 5 and matured using poly(I:C) at 5 µg/mL/$10^6$ DCs (Amersham). Secretion of IL-12p70, TNFα, IL-1β, IL-6, IL-8 and IL-10 was assessed on both immature and mature DCs using the Human Inflammatory Cytokine Cytometric Bead Array (BD Pharmingen).

Enzyme-Linked Immunosorbent Assay

Activation of T cell clones (10,000 cells/100 µL/well), polyclonal T cell populations (100,000 cells/100 µL/well), and DCs (50,000 cells/100 µL/well) can be determined by ELISA. IFNγ (BioSource), TNFα (BioSource), IL-4 (BioSource), IFNβ (VeriKine; PBL interferon source) and MCP-3 (DuoSet; R&D Systems) contents in supernatants were measured according to the manufacturer's instructions. p50 was measured in cytosolic and nuclear fractions (fractions separated using the nuclear separation kit from Active motif) by ELISA (Active motif).

Intracellular Staining

T-bet and GATA-3 expression was measured on resting T cells. Cells were fixed (4% paraformaldehyde for 10 min at RT), permeabilized with 0.1% saponin, and stained for intracellular transcription factors. Cytokine production by T cells was also assessed by intracellular staining. T cells were stimulated with 2 µM overlapping peptides. After 1 h, 10 µg/mL brefeldin A was added to the cells. Five hours later, T cells were stained for surface markers, fixed, permeabilized, and stained for intracellular cytokines (TNFα, IFNγ, IL-2, perforin, granzymeB, IL-4, IL-5, IL-10, IL-13 and IL-17). Antigen-specificity was defined by the percentage of cells secreting cytokine as long as it exceeded background (cytokine-secreting cells in the absence of peptide stimulation) by more than twofold and consisted of more than 0.5% of responding cells following subtraction of background for at least one cytokine. It was not uncommon to find relatively high background levels of IL-4 and TNFα producing T cells, likely due to the fact that these highly sensitive cells continued to produce cytokine up to 2-3 weeks after stimulation.

HEK-Blue™-hTLR2 Cells were from Invivogen. HEK-Blue™-hTLR2 Cells were obtained by co-transfection of the hTLR2 and SEAP (secreted embryonic alkaline phosphatase) reporter genes into HEK293 cells. The SEAP reporter gene is placed under the control of NF-κB-binding sites. Stimulation with a TLR2 ligand activates NF-κB which induces the production of SEAP. After overnight stimulation, levels of SEAP can be easily determined with QUANTI-Blue™ a detection medium that turns purple/blue (by determining the optical density at 655 nm) in the presence of alkaline phosphatase.

Statistical Analysis

Separate analyses were performed for each experiment individually. Analyses take into account paired observations within donors when appropriate (e.g., MMP-2 vs no MMP-2, active vs inactive, active vs peptides). For three-group comparisons (e.g., MMP-2, Melan-A, NY-ESO-1), analyses of variance were performed for an overall comparison among independent groups, and t-tests were then used for specific pairwise comparisons between groups. Within each analysis, p-values were adjusted for multiple comparisons using a Bonferroni correction. For analyses in which each of two groups was compared to a third group (i.e., two comparisons, with no overall test of the three groups), two t-tests were performed, using the Bonferroni adjustment for the two analyses. Two-sided statistical tests were performed at an overall alpha-level of 0.05, with adjustments for multiple comparisons, as described above. Details for each analysis are provided in the Brief Description of the Drawings.

RESULTS

Identification of the MMP-2-Triggered Receptor Leading to OX40L Expression

Because the ox40l gene has a promoter region containing 2 atypical NF-kB binding sites [Arima et al. *Sci Signal* 3, (2010)], the present inventors investigated whether MMP-2 could activate the NF-κB pathway as well. Indeed, results presented herein demonstrate that MMP-2 triggers p50 translocation in the nucleus (FIGS. 2A-B) and NEMO activation (FIG. 2C), two components of the NF-κB pathway. MMP-2-treated DCs also secrete inflammatory cytokines (IL-1β, IL-6, IL-8, TNFα) known to be under the control of NF-κB (FIG. 2D). Altogether, these results show that MMP-2 activates the NF-κB pathway in DCs.

Using TLR-transfected engineered HEK cells as reporter cell lines, the present inventors found that MMP-2 activates NF-κB through TLR-2 triggering (FIG. 4). These reporter cells, called HEK-Blue™-hTLR2 Cells, are designed for studying the stimulation of human TLR-2 by monitoring the activation of NF-κB. HEK-Blue™-hTLR2 Cells were obtained by co-transfection of the hTLR2 and SEAP (secreted embryonic alkaline phosphatase) reporter genes into HEK293 cells. The SEAP reporter gene is placed under the control of NF-κB-binding sites. Stimulation with a TLR2 ligand activates NF-κB which induces the production of SEAP. Levels of SEAP can be easily determined with QUANTI-Blue™ a detection medium that turns purple/blue in the presence of alkaline phosphatase.

Accordingly, TLR-2 transfected engineered HEK reporter cell lines are set forth as an exemplary component of a cell based screening assay to identify modulators of MMP-2/TLR-2 interaction.

Determination of the Minimal MMP-2 Sequence Triggering TLR2

Both active MMP-2 and heat-inactivated (HI) MMP-2 induce OX40L expression (FIG. 2C) and NF-κB activation (FIGS. 2A, 2B and 3) at similar levels in DCs, demonstrating that the protein conformation is not key for TLR-2 triggering/binding. Data presented in FIGS. 3 and 5 suggest that the minimal MMP-2 peptide sequence needed for TLR-2 triggering/binding is over 20 amino acids long and is likely to be located in the first two-thirds of MMP-2 (amino acids 1-445 of SEQ ID NO: 1), because PEX, the last third of MMP-2 (amino acids 445-635 of SEQ ID NO: 1), did not trigger TLR-2 activation. See FIG. 6 for additional information pertaining to the MMP-2 20-mers tested in pools and assayed as shown in FIG. 5. Further to the objective of delineating the minimal MMP-2 peptide sequence needed for TLR-2 triggering/binding, the present inventors are generating various recombinant fragments of MMP-2 and testing their ability to induce OX40L expression and NF-κB activation in DCs as well as in TLR-2-transfected HEK cells. Such fragments will serve to identify sub-fragments of MMP-2 that retain the ability of full length MMP-2 to activate TLR-2, as assayed by increased TLR-2 signaling, NF-κB activation and OX40L expression. Exemplary MMP-2 fragments comprise or consist of at least two of the 20-mer MMP-2 peptides described herein or consist of the amino terminal two-thirds of full length MMP-2 or smaller fragments thereof.

Figure 7:
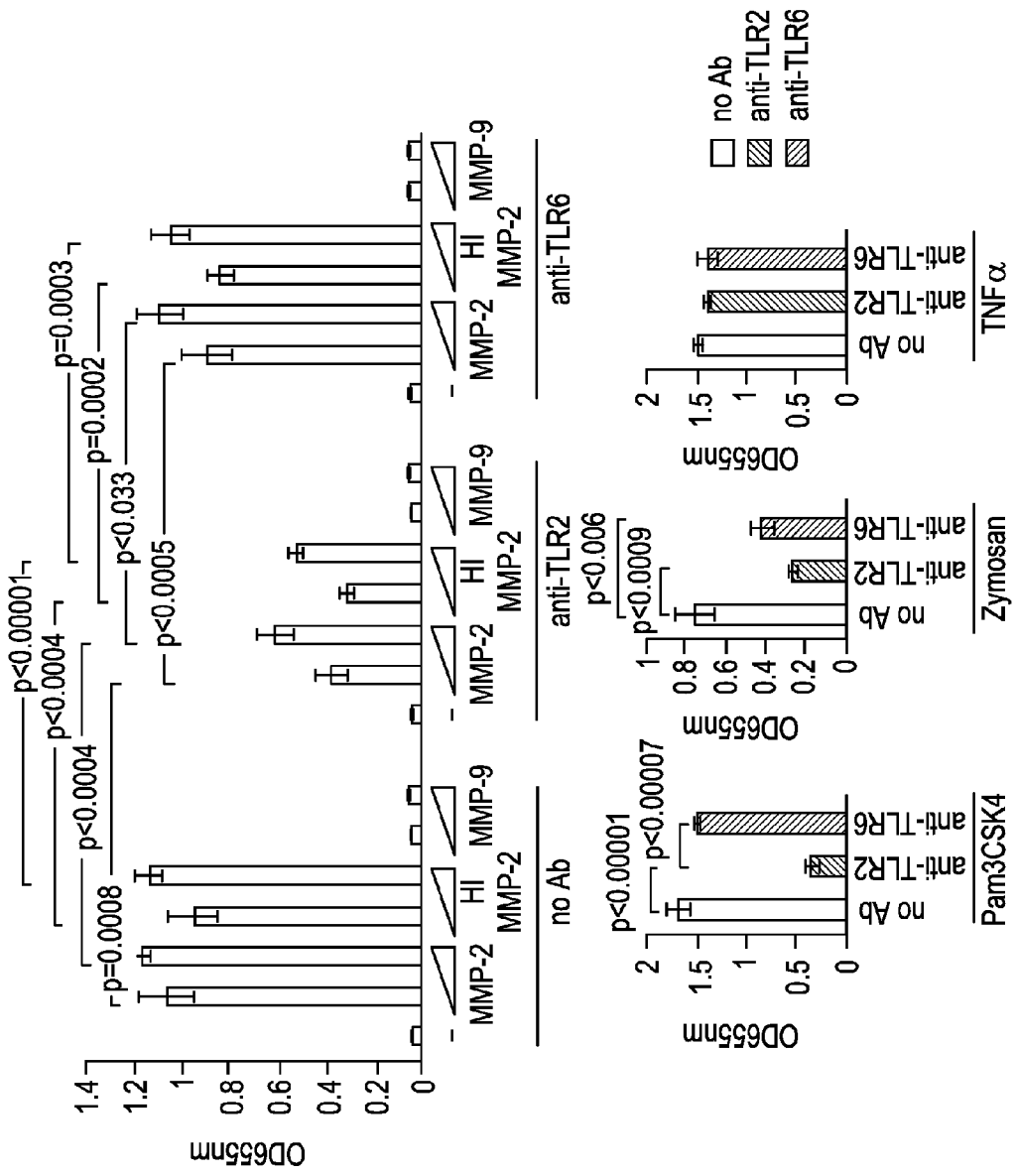
FIG. 7 shows that MMP-2 activates NF-κB signaling by triggering TLR2 signaling.

Results depicted in FIG. 7 reveal that a blocking antibody specific for TLR6 blocks activation by zymosan but not MMP-2, demonstrating that with regards to MMP-2 activation, TLR2 does not need to cooperate with TLR6. The blocking antibody specific for TLR6 is a polyclonal antibody specific for human TLR2 and was purchased from InvivoGen (Catalog # pab-hstlr2). Controls using TLR2/1 (Pam) and TLR2/6 (Zymosan) agonists demonstrate that both antibodies are functionally active in the assay used. In light of the above, FIG. 7 shows that MMP-2 activates NF-κB signaling via TLR2 signaling.

MMP-2 Binds to the TLR2/MyD88 Complex

Figure 8A:
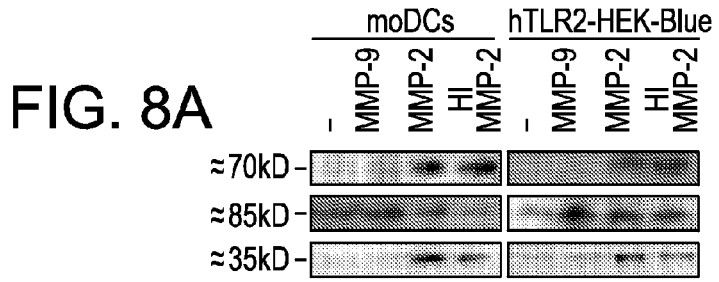
FIG. 8 shows that MMP-2 and TLR2 can be co-immunoprecipitated. $10^6$ moDCs/lane or TLR2-transfected HEK cells were incubated for 20 min with or without 5 μg/ml MMP-2 or MMP-9 before being lysed. TLR2 A) and MMP-2 B) were immunoprecipitated using specific antibodies and protein G-agarose. Western blots for MMP-2 (≈70 kD), TLR2 (≈85 kD) and MyD88 (≈35 kD) were then performed. C and D) depict band intensities (mean of 3 independent experiments±s.d.), which are represented as a percentage of the band intensity corresponding to untreated cells. Two-tailed Student's t-tests were used to compare MMP-2- to MMP-9-treated cells. p values≤0.05 (*) were considered statistically significant.
Figure 8B:
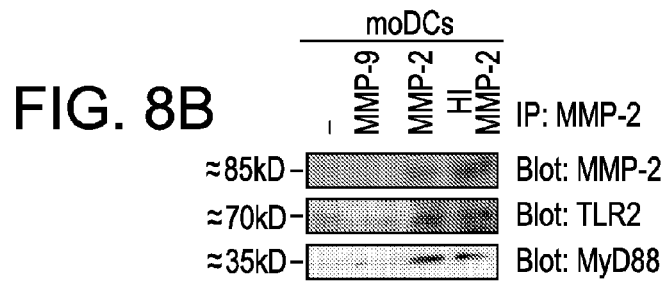
Figure 8C:
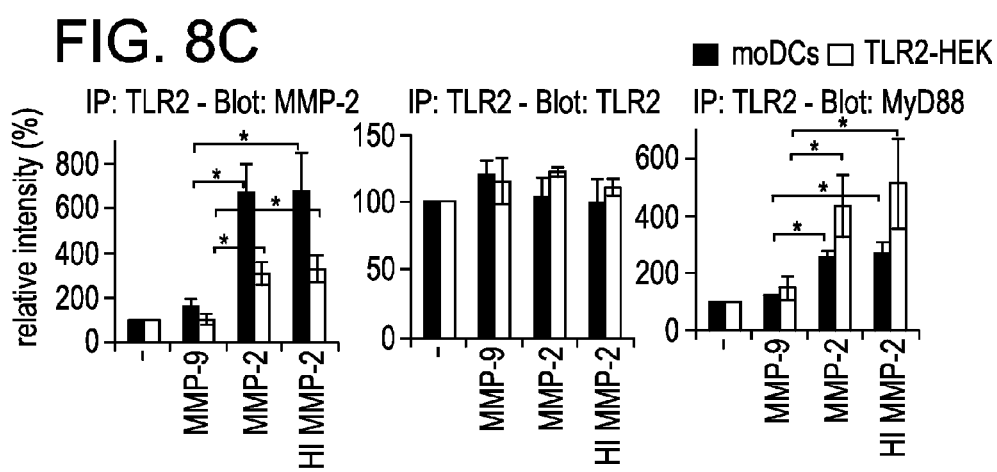
Figure 8D:
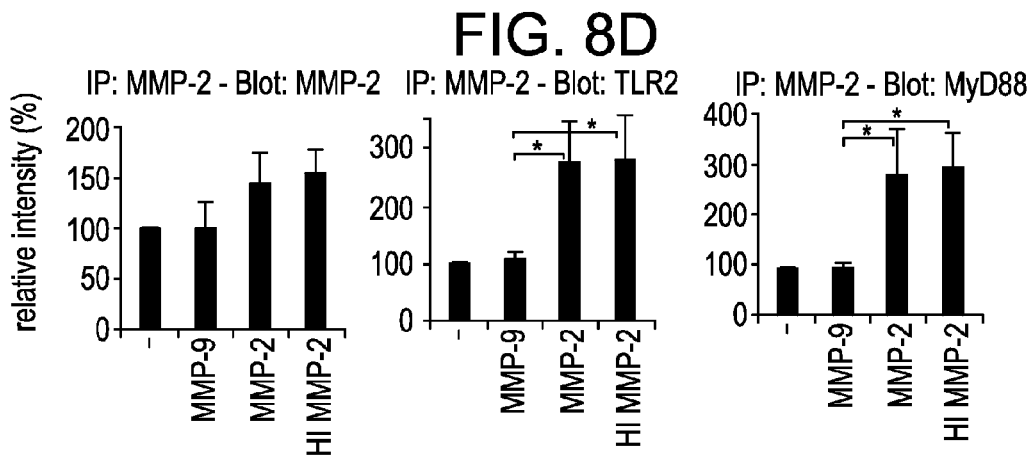

To assess whether MMP-2 directly interacts with TLR2, moDCs and TLR2-transfected HEK cells were utlized. As shown in FIG. 8, both MMP-2 and MyD88 immunoprecipitated (n=3; p<0.05 compared to MMP-9-treated cells) with TLR2 when cells were pre-treated with MMP-2 (active or inactive), but not with MMP-9 (FIG. 8A,C). Similarly, TLR2 and MyD88 immunoprecipitated (n=3; p<0.05 compared to MMP-9-treated cells) with MMP-2 when moDCs were pre-treated with MMP-2 (FIG. 8B,D). These results strongly suggest that MMP-2 directly interacts with and subsequently activates TLR2, leading to the recruitment of MyD88 to the intracellular domain of TLR2, to the plasma membrane.

Figure 9C:
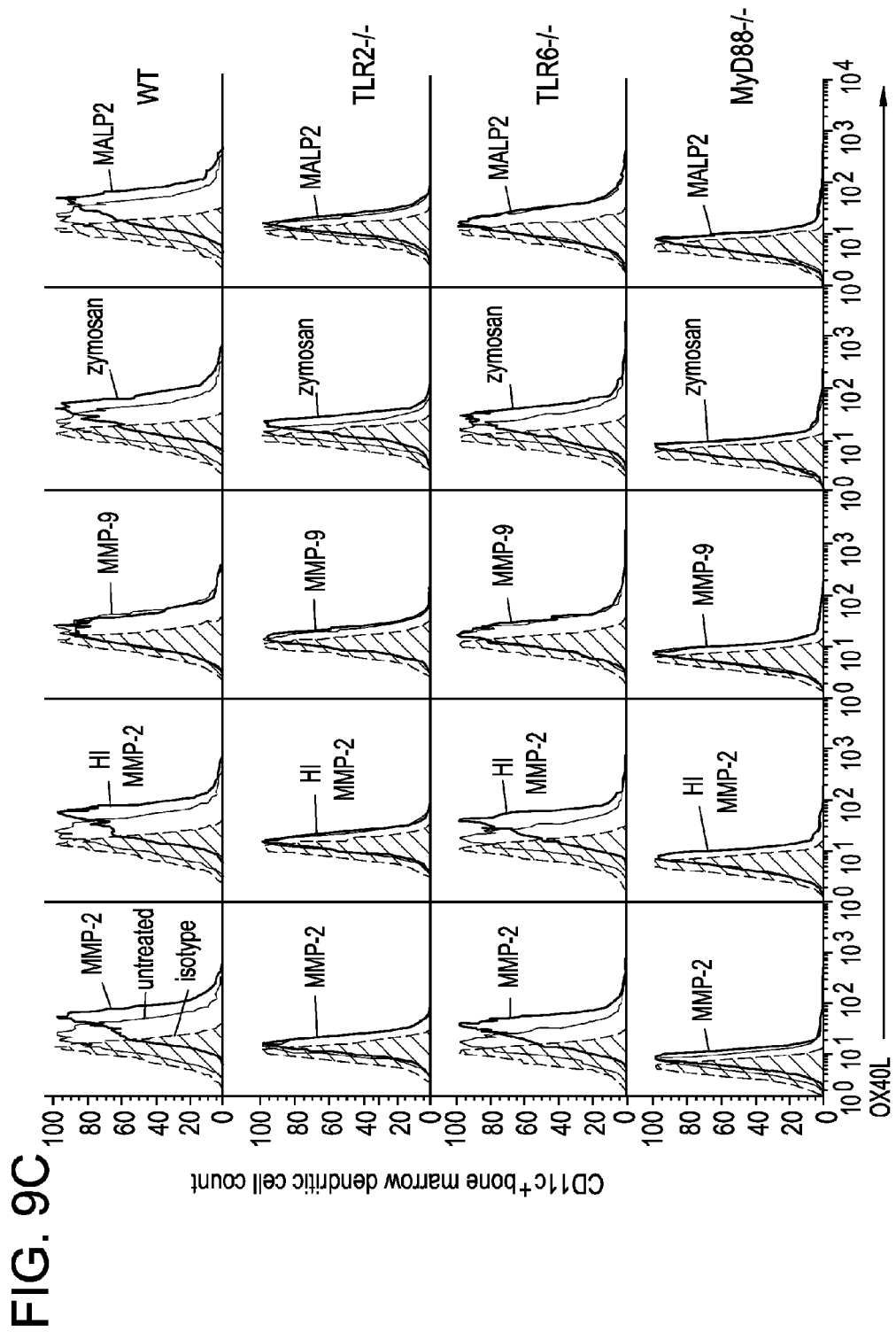
FIG. 9 shows that murine MMP-2 activates bone-marrow-derived DCs in a TLR2- and MyD88-dependent manner. Bone-marrow-derived DCs from wild-type, TLR2$^{-/-}$, TLR6$^{-/-}$ or MyD88$^{-/-}$ C57/BL6 mice (3 mice pooled/condition) were incubated overnight with 5 μg/ml mMMP-2 or mMMP-9 as well as TLR agonists for controls. TNFα (A) and IL-6 (B) were measured by cytometric bead array analysis. Results are represented as a mean of triplicates±s.d. Two-tailed Student's t-tests were used for specific pairwise comparisons between conditions. p values≤0.05 (*) were considered statistically significant. C) Murine OX40L expression was assessed 2 days later by immunostaining.

Using TLR-deficient C57/BL6 mice, the present inventors next formally demonstrated that MMP-2 requires TLR2 to activate DCs. Bone-marrow-derived DCs (BM-DCs) were generated and cultured with murine MMP-2 or various controls. In the presence of MMP-2 (active or inactive), wild-type BM-DCs as well as TLR6$^{-/-}$ BM-DCs secreted inflammatory cytokines such as TNFα (FIG. 9A) or IL-6 (FIG. 9B) and up-regulated OX40L (FIG. 9C). On the other hand, TLR2$^{-/-}$ and MyD88$^{-/-}$ BM-DCs were not activated by MMP-2 (n=3; p<0.02 compared to wild-type mice) (FIG. 9A-C). These results were also confirmed using CD11c-purified splenic DCs. Therefore, MMP-2 induces DCs to produce inflammatory cytokines and to up-regulate OX40L in a TLR2/MyD88-dependent manner.

Development of Molecules Blocking the MMP-2 Signaling Leading to OX40L Expression Exploiting a high throughput screening method based on the usage of the TLR-2-transfected engineered HEK cells, small MMP-2 peptides located in the minimal MMP-2 sequence responsible for TLR-2 triggering will be screened for their ability to block signaling. Since the three dimensional structures of MMP-2 and TLR2 are known, three dimensional modeling can also be used to design small molecules with the capacity to prevent MMP-2/TLR2 interaction/binding. In this case, candidate molecules will be tested as above using TLR-2-transfected HEK cells. The level of inhibition of NF-κB signaling and OX40L expression and subsequent $T_H2$ immune responses will also be assessed in the presence of the identified small molecule. T cells generated in the presence of such small molecule inhibitors are expected to display a $T_H1$ phenotype, i.e. secreting anti-tumoral IFNγ and exerting cytolytic capabilities that target tumor cells.

DISCUSSION

Traditional cancer treatments, such as chemotherapy and radiotherapy, are frequently ineffective and induce potent debilitating side effects, some of which are potentially deadly. Immune therapies have been found to be much safer, but still need to be optimized. The main barrier to the design of effective immunotherapies is local immunosuppression induced by the tumor. As described herein, the present inventors have elucidated an immunosuppressive role of MMP-2 in inducing ineffective/detrimental $T_H2$ immune responses and defined the underlying mechanism through which MMP-2 mediates this role, namely via TLR2 triggering. Identification/design of a small molecule(s) that block MMP-2/TLR2 interaction/binding presents an opportunity to develop therapeutic agents that have the ability to re-set a patient's immune system to promote strong, effective anti-tumor $T_H1$ responses. The broad expression of MMP-2 in most cancer types indicates such therapeutic agents would be efficacious in the treatment of virtually any cancer.

REFERENCES

Botella-Estrada, R., Escudero, M., O'Connor, J. E., Nagore, E., Fenollosa, B., Sanmartin, O., Requena, C., and Guillen, C. (2005). Cytokine production by peripheral lymphocytes in melanoma. Eur Cytokine Netw 16, 47-55.

Brooks, P. C., Silletti, S., von Schalscha, T. L., Friedlander, M., and Cheresh, D. A. (1998). Disruption of angiogenesis by PEX, a noncatalytic metalloproteinase fragment with integrin binding activity. Cell 92, 391-400.

Brooks, P. C., Stromblad, S., Sanders, L. C., von Schalscha, T. L., Aimes, R. T., Stetler-Stevenson, W. G., Quigley, J. P., and Cheresh, D. A. (1996). Localization of matrix metalloproteinase MMP-2 to the surface of invasive cells by interaction with integrin alpha v beta 3. Cell 85, 683-693.

Choi, W. S., Jeon, O. H., Kim, H. H., and Kim, D. S. (2008). MMP-2 regulates human platelet activation by interacting with integrin alphaIIbbeta3. J Thromb Haemost 6, 517-523.

Coulie, P. G., and van der Bruggen, P. (2003). T-cell responses of vaccinated cancer patients. Curr Opin Immunol 15, 131-137.

Decker, T., Muller, M., and Stockinger, S. (2005). The yin and yang of type I interferon activity in bacterial infection. Nat Rev Immunol 5, 675-687.

Dreno, B., Nguyen, J. M., Khammari, A., Pandolfino, M. C., Tessier, M. H., Bercegeay, S., Cassidanius, A., Lemarre, P., Billaudel, S., Labarriere, N., et al. (2002). Randomized trial of adoptive transfer of melanoma tumor-infiltrating lymphocytes as adjuvant therapy for stage III melanoma. Cancer Immunol Immunother 51, 539-546.

Emonard, H., Belton, G., Troeberg, L., Berton, A., Robinet, A., Henriet, P., Marbaix, E., Kirkegaard, K., Patthy, L., Eeckhout, Y., et al. (2004). Low density lipoprotein receptor-related protein mediates endocytic clearance of pro-MMP-2.TIMP-2 complex through a thrombospondin-independent mechanism. J Biol Chem 279, 54944-54951.

Everts, B., Perona-Wright, G., Smits, H. H., Hokke, C. H., van der Ham, A. J., Fitzsimmons, C. M., Doenhoff, M. J., van der Bosch, J., Mohrs, K., Haas, H., et al. (2009). Omega-1, a glycoprotein secreted by Schistosoma mansoni eggs, drives Th2 responses. J Exp Med 206, 1673-1680.

Falcone, F. H., Dahinden, C. A., Gibbs, B. F., Noll, T., Amon, U., Hebestreit, H., Abrahamsen, O., Klaucke, J., Schlaak, M., and Haas, H. (1996). Human basophils release interleukin-4 after stimulation with Schistosoma mansoni egg antigen. Eur J Immunol 26, 1147-1155.

Gautier, G., Humbert, M., Deauvieau, F., Scuiller, M., Hiscott, J., Bates, E. E., Trinchieri, G., Caux, C., and Garrone, P. (2005). A type I interferon autocrineparacrine loop is involved in Toll-like receptor-induced interleukin-12p70 secretion by dendritic cells. J Exp Med 201, 1435-1446.

Godefroy, E., Moreau-Aubry, A., Diez, E., Dreno, B., Jotereau, F., and Guilloux, Y. (2005). alpha v beta3-dependent cross-presentation of matrix metalloproteinase-2 by melanoma cells gives rise to a new tumor antigen. J Exp Med 202, 61-72.

Godefroy, E., Scotto, L., Souleimanian, N. E., Ritter, G., Old, L. J., Jotereau, F., Valmori, D., and Ayyoub, M. (2006). Identification of two Melan-A CD4+ T cell epitopes presented by frequently expressed MHC class II alleles. Clin Immunol 121, 54-62.

Godefroy, E., Wang, Y., Souleimanian, N. E., Scotto, L., Stevanovic, S., Chen, Y. T., Valmori, D., and Ayyoub, M. (2007). Assessment of CD4+ T cells specific for the tumor antigen SSX-1 in cancer-free individuals. Cancer Immunol Immunother 56, 1183-1192.

Grobe, K., Becker, W. M., Schlaak, M., and Petersen, A. (1999). Grass group I allergens (beta-expansins) are novel, papain-related proteinases. Eur J Biochem 263, 33-40.

Hirohashi, Y., Torigoe, T., Inoda, S., Kobayasi, J., Nakatsugawa, M., Mori, T., Hara, I., and Sato, N. (2009). The functioning antigens: beyond just as the immunological targets. Cancer Sci 100, 798-806.

Ito, T., Wang, Y. H., Duramad, O., Hori, T., Delespesse, G. J., Watanabe, N., Qin, F. X., Yao, Z., Cao, W., and Liu, Y. J. (2005). TSLP-activated dendritic cells induce an inflammatory T helper type 2 cell response through OX40 ligand. J Exp Med 202, 1213-1223.

Itoh, T., Tanioka, M., Yoshida, H., Yoshioka, T., Nishimoto, H., and Itohara, S. (1998). Reduced angiogenesis and tumor progression in gelatinase A-deficient mice. Cancer Res 58, 1048-1051.

Jankovic, D., Kullberg, M. C., Noben-Trauth, N., Caspar, P., Paul, W. E., and Sher, A. (2000). Single cell analysis reveals that IL-4 receptor/Stat6 signaling is not required for the in vivo or in vitro development of CD4+ lymphocytes with a Th2 cytokine profile. J Immunol 164, 3047-3055.

Kessenbrock, K., Plaks, V., and Werb, Z. (2010). Matrix metalloproteinases: regulators of the tumor microenvironment. Cell 141, 52-67.

Khammari, A., Nguyen, J. M., Pandolfino, M. C., Quereux, G., Brocard, A., Bercegeay, S., Cassidanius, A., Lemarre, P., Volteau, C., Labarriere, N., et al. (2007). Longterm follow-up of patients treated by adoptive transfer of melanoma tumor-infiltrating lymphocytes as adjuvant therapy for stage III melanoma. Cancer Immunol Immunother 56, 1853-1860.

Kheradmand, F., Kiss, A., Xu, J., Lee, S. H., Kolattukudy, P. E., and Corry, D. B. (2002). A protease-activated pathway underlying Th cell type 2 activation and allergic lung disease. J Immunol 169, 5904-5911.

Labarriere, N., Pandolfino, M. C., Gervois, N., Khammari, A., Tessier, M. H., Dreno, B., and Jotereau, F. (2002). Therapeutic efficacy of melanoma-reactive TIL injected in stage III melanoma patients. Cancer Immunol Immunother 51, 532-538.

Lauerova, L., Dusek, L., Simickova, M., Kocak, I., Vagundova, M., Zaloudik, J., and Kovarik, J. (2002). Malignant melanoma associates with Th1/Th2 imbalance that coincides with disease progression and immunotherapy response. Neoplasma 49, 159-166.

Liotta, L. A., Tryggvason, K., Garbisa, S., Hart, I., Foltz, C. M., and Shafie, S. (1980). Metastatic potential correlates with enzymatic degradation of basement membrane collagen. Nature 284, 67-68.

Liu, Y. J. (2006). Thymic stromal lymphopoietin: master switch for allergic inflammation. J Exp Med 203, 269-273.

Liu, Y. J., Soumelis, V., Watanabe, N., Ito, T., Wang, Y. H., Malefyt Rde, W., Omori, M., Zhou, B., and Ziegler, S. F. (2007). TSLP: an epithelial cell cytokine that regulates T cell differentiation by conditioning dendritic cell maturation. Annu Rev Immunol 25, 193-219.

Loose, D., and Van de Wiele, C. (2009). The immune system and cancer. Cancer Biother Radiopharm 24, 369-376.

McCarter, M., Clarke, J., Richter, D., and Wilson, C. (2005). Melanoma skews dendritic cells to facilitate a T helper 2 profile. Surgery 138, 321-328.

McKerrow, J. H., Caffrey, C., Kelly, B., Loke, P., and Sajid, M. (2006). Proteases in parasitic diseases. Annu Rev Pathol 1, 497-536.

Minkis, K., Kavanagh, D. G., Alter, G., Bogunovic, D., O'Neill, D., Adams, S., Pavlick, A., Walker, B. D., Brockman, M. A., Gandhi, R. T., et al. (2008). Type 2 Bias of T cells expanded from the blood of melanoma patients switched to type 1 by IL-12p70 mRNA-transfected dendritic cells. Cancer Res 68, 9441-9450.

Moser, M., and Murphy, K. M. (2000). Dendritic cell regulation of TH1-TH2 development. Nat Immunol 1, 199-205.

Mosmann, T. R., and Coffman, R. L. (1989). TH1 and TH2 cells: different patterns of lymphokine secretion lead to different functional properties. Annu Rev Immunol 7, 145-173.

Nishimura, T., Iwakabe, K., Sekimoto, M., Ohmi, Y., Yahata, T., Nakui, M., Sato, T., Habu, S., Tashiro, H., Sato, M., et al. (1999). Distinct role of antigen-specific T helper type 1 (Th1) and Th2 cells in tumor eradication in vivo. J Exp Med 190, 617-627.

Nishimura, T., Nakui, M., Sato, M., Iwakabe, K., Kitamura, H., Sekimoto, M., Ohta, A., Koda, T., and Nishimura, S. (2000). The critical role of Th1-dominant immunity in tumor immunology. Cancer Chemother Pharmacol 46 Suppl, S52-61.

Ocmant, A., Peignois, Y., Mulier, S., Hanssens, L., Michils, A., and Schandene, L. (2007). Flow cytometry for basophil activation markers: the measurement of CD203c up-regulation is as reliable as CD63 expression in the diagnosis of cat allergy. J Immunol Methods 320, 40-48.

Oh, K., Shen, T., Le Gros, G., and Min, B. (2007). Induction of Th2 type immunity in a mouse system reveals a novel immunoregulatory role of basophils. Blood 109, 2921-2927. Rosenberg, S. A. (2004). Shedding light on immunotherapy for cancer. N Engl J Med 350, 1461-1463.

Severa, M., Remoli, M. E., Giacomini, E., Ragimbeau, J., Lande, R., Uze, G., Pellegrini, S., and Coccia, E. M. (2006). Differential responsiveness to IFN-alpha and IFN-beta of human mature DC through modulation of IFNAR expression. J Leukoc Biol 79, 1286-1294.

So, T., Song, J., Sugie, K., Altman, A., and Croft, M. (2006). Signals from OX40 regulate nuclear factor of activated T cells c1 and T cell helper 2 lineage commitment. Proc Natl Acad Sci USA 103, 3740-3745.

Sokol, C. L., Barton, G. M., Farr, A. G., and Medzhitov, R. (2008). A mechanism for the initiation of allergen-induced T helper type 2 responses. Nat Immunol 9, 310-318.

Sokol, C. L., Chu, N. Q., Yu, S., Nish, S. A., Laufer, T. M., and Medzhitov, R. (2009). Basophils function as antigen-presenting cells for an allergen-induced T helper type 2 response. Nat Immunol 10, 713-720.

Soumelis, V., and Liu, Y. J. (2004). Human thymic stromal lymphopoietin: a novel epithelial cell-derived cytokine and a potential key player in the induction of allergic inflammation. Springer Semin Immunopathol 25, 325-333.

Soumelis, V., Reche, P. A., Kanzler, H., Yuan, W., Edward, G., Homey, B., Gilliet, M., Ho, S., Antonenko, S., Lauerma, A., et al. (2002). Human epithelial cells trigger dendritic cell mediated allergic inflammation by producing TSLP. Nat Immunol 3, 673-680.

Stefanidakis, M., Bjorklund, M., Ihanus, E., Gahmberg, C. G., and Koivunen, E. (2003). Identification of a negatively charged peptide motif within the catalytic domain of progelatinases that mediates binding to leukocyte beta 2 integrins. J Biol Chem 278, 34674-34684.

Steinfelder, S., Andersen, J. F., Cannons, J. L., Feng, C. G., Joshi, M., Dwyer, D., Caspar, P., Schwartzberg, P. L., Sher, A., and Jankovic, D. (2009). The major component in schistosome eggs responsible for conditioning dendritic cells for Th2 polarization is a T2 ribonuclease (omega-1). J Exp Med 206, 1681-1690.

Swain, S. L., Weinberg, A. D., English, M., and Huston, G. (1990). IL-4 directs the development of Th2-like helper effectors. J Immunol 145, 3796-3806.

Szabo, S. J., Kim, S. T., Costa, G. L., Zhang, X., Fathman, C. G., and Glimcher, L. H. (2000). A novel transcription factor, T-bet, directs Th1 lineage commitment. Cell 100, 655-669.

Tatsumi, T., Kierstead, L. S., Ranieri, E., Gesualdo, L., Schena, F. P., Finke, J. H., Bukowski, R. M., Mueller-Berghaus, J., Kirkwood, J. M., Kwok, W. W., et al. (2002). Disease-associated bias in T helper type 1 (Th1)/Th2 CD4(+) T cell responses against MAGE-6 in HLA-DRB10401(+) patients with renal cell carcinoma or melanoma. J Exp Med 196, 619-628.

Watanabe, N., Hanabuchi, S., Soumelis, V., Yuan, W., Ho, S., de Waal Malefyt, R., and Liu, Y. J. (2004). Human thymic stromal lymphopoietin promotes dendritic cell-mediated CD4+ T cell homeostatic expansion. Nat Immunol 5, 426-434.

Westermarck, J., and Kahari, V. M. (1999). Regulation of matrix metalloproteinase expression in tumor invasion. Faseb J 13, 781-792.

Yee, C., Thompson, J. A., Roche, P., Byrd, D. R., Lee, P. P., Piepkorn, M., Kenyon, K., Davis, M. M., Riddell, S. R., and Greenberg, P. D. (2000). Melanocyte destruction after antigen-specific immunotherapy of melanoma: direct evidence of t cell-mediated vitiligo. J Exp Med 192, 1637-1644.

Yu, Q., Sharma, A., Oh, S. Y., Moon, H. G., Hossain, M. Z., Salay, T. M., Leeds, K. E., Du, H., Wu, B., Waterman, M. L., et al. (2009). T cell factor 1 initiates the T helper type 2 fate by inducing the transcription factor GATA-3 and repressing interferon-gamma. Nat Immunol 10, 992-999.

What is claimed is:

1. A method for screening to identify a modulator of matrix metalloproteinase protein-2 (MMP-2) mediated activation of toll-like receptor-2 (TLR-2), the method comprising: contacting a composition comprising TLR-2 and MMP-2 with a candidate modulator agent, wherein MMP-2 is a protein comprising or consisting of SEQ ID NO: 1 or a protein at least 90% identical to SEQ ID NO: 1, wherein said protein at 90% identical to SEQ ID NO: 1 activates TLR-2, and measuring direct interaction of TLR-2 and MMP-2 to assess TLR-2/MMP-2 interaction levels in the presence of the candidate modulator agent, wherein detecting a change in TLR-2/MMP-2 interaction levels in the presence of the candidate modulator agent relative to TLR-2/MMP-2 interaction levels in the presence of a control agent identifies a modulator of MMP-2 mediated activation of TLR-2.

2. The method of claim 1, wherein the change detected in the presence of the candidate modulator agent is a reduction in TLR-2/MMP-2 interaction levels, thereby identifying the candidate modulator agent as an inhibitor of MMP-2 mediated activation of TLR-2.

3. The method of claim 1, wherein the TLR-2 is expressed on a cell.

4. The method of claim 3, wherein the cell is transfected to express TLR-2.

5. The method of claim 3, wherein the cell expressing TLR-2 is contacted with the MMP-2 protein.

6. The method of claim 3, wherein the change in TLR-2/MMP-2 interaction levels is detected further by measuring nuclear factor-κB (NF-κB) signaling by assaying NEMO activation or p50 translocation into the nucleus, secretion of inflammatory cytokines by detecting levels of inflammatory cytokine proteins in supernatants of the cell, or OX40 ligand (OX40L) over-expression on the cell.

7. The method of claim 6, wherein the change detected in the presence of the candidate modulator agent is a reduction in NEMO activation or p50 translocation into the nucleus, a reduction in the secretion of inflammatory $T_H2$ cytokines, an increase in the secretion of $T_H1$ cytokines, or a reduction in OX40 ligand (OX40L) over-expression on the cell.

8. The method of claim 7, wherein the inflammatory $T_H2$ cytokines are selected from the group consisting of IL-1β, IL-4, IL-6, IL-8, IL-13, and TNFα, and the $T_H1$ cytokines are selected from the group consisting of IFNγ and IL-2.

9. The method of claim 1, wherein the TLR-2 is an isolated protein.

10. The method of claim 9, wherein the TLR-2 is contacted with the MMP-2 protein.

11. The method of claim 1, wherein the candidate modulator agent is a small organic molecule, a protein or peptide, a nucleic acid, a carbohydrate, or an antibody.

12. A method for screening to identify a modulator of matrix metalloproteinase protein-2 (MMP-2) mediated activation of toll-like receptor-2 (TLR-2), the method comprising: contacting at least one cell expressing TLR-2 with MMP-2 and a candidate modulator agent, wherein MMP-2 is a protein comprising or consisting of SEQ ID NO: 1 or a protein at least 90% identical to SEQ ID NO: 1, wherein said protein at 90% identical to SEQ ID NO: 1 activates TLR-2, and assessing interaction of TLR-2 expressed on the at least one cell and the MMP-2 in contact with the TLR-2 expressed on the at least one cell in the presence of the candidate modulator agent, wherein detecting a change in TLR-2/MMP-2 interaction levels in the presence of the candidate modulator agent relative to TLR-2/MMP-2 interaction levels in the presence of a control agent identifies a modulator of MMP-2 mediated activation of TLR-2.

13. The method of claim 12, wherein the change detected in the presence of the candidate modulator agent is a reduction in TLR-2/MMP-2 interaction levels, thereby identifying the candidate modulator agent as an inhibitor of MMP-2 mediated activation of TLR-2.

14. The method of claim 12, wherein the at least one cell is transfected to express TLR-2.

15. The method of claim 12, wherein the change in TLR-2/MMP-2 interaction levels is detected by measuring nuclear factor-κB (NF-κB) signaling by assaying NEMO activation or p50 translocation into the nucleus, secretion of inflammatory cytokines by detecting levels of inflammatory cytokine proteins in supernatants of the at least one cell, or OX40 ligand (OX40L) over-expression on the cell.

16. The method of claim 15, wherein the change detected in the presence of the candidate modulator agent is a reduction NEMO activation or p50 translocation into the nucleus, a reduction in the secretion of inflammatory $T_H2$ cytokines, an increase in the secretion of $T_H1$ cytokines, or a reduction in OX40 ligand (OX40L) over-expression on the cell.

17. The method of claim 15, wherein the candidate modulator agent is a small organic molecule, a protein or peptide, a nucleic acid, a carbohydrate, or an antibody.

* * * * *

UNITED STATES PATENT AND TRADEMARK OFFICE
CERTIFICATE OF CORRECTION

PATENT NO. : 9,539,315 B2
APPLICATION NO. : 14/343123
DATED : January 10, 2017
INVENTOR(S) : Emmanuelle Godefroy et al.

It is certified that error appears in the above-identified patent and that said Letters Patent is hereby corrected as shown below:

At Column 1, Lines 18-21, replace:
"The research leading to the present invention was supported, at least in part, by National Institutes of Health Grant Nos. R01 AI071078 and 1R01AI061684. Accordingly, the Government has certain rights in the invention."
With:
--This invention was made with government support under grant numbers AI061684 and AI071078 awarded by the National Institutes of Health. The government has certain rights in the invention.--

Signed and Sealed this
Twenty-second Day of October, 2019

Andrei Iancu
*Director of the United States Patent and Trademark Office*

SEQUENCE LISTING

<160> NUMBER OF SEQ ID NOS: 25

<210> SEQ ID NO 1
<211> LENGTH: 660
<212> TYPE: PRT
<213> ORGANISM: Homo sapiens

<400> SEQUENCE: 1

```
Met Glu Ala Leu Met Ala Arg Gly Ala Leu Thr Gly Pro Leu Arg Ala
 1               5                   10                  15

Leu Cys Leu Leu Gly Cys Leu Leu Ser His Ala Ala Ala Ala Pro Ser
                20                  25                  30

Pro Ile Ile Lys Phe Pro Gly Asp Val Ala Pro Lys Thr Asp Lys Glu
            35                  40                  45

Leu Ala Val Gln Tyr Leu Asn Thr Phe Tyr Gly Cys Pro Lys Glu Ser
    50                  55                  60

Cys Asn Leu Phe Val Leu Lys Asp Thr Leu Lys Lys Met Gln Lys Phe
65                  70                  75                  80

Phe Gly Leu Pro Gln Thr Gly Asp Leu Asp Gln Asn Thr Ile Glu Thr
                85                  90                  95

Met Arg Lys Pro Arg Cys Gly Asn Pro Asp Val Ala Asn Tyr Asn Phe
            100                 105                 110

Phe Pro Arg Lys Pro Lys Trp Asp Lys Asn Gln Ile Thr Tyr Arg Ile
        115                 120                 125

Ile Gly Tyr Thr Pro Asp Leu Asp Pro Glu Thr Val Asp Asp Ala Phe
    130                 135                 140

Ala Arg Ala Phe Gln Val Trp Ser Asp Val Thr Pro Leu Arg Phe Ser
145                 150                 155                 160

Arg Ile His Asp Gly Glu Ala Asp Ile Met Ile Asn Phe Gly Arg Trp
                165                 170                 175

Glu His Gly Asp Gly Tyr Pro Phe Asp Gly Lys Asp Gly Leu Leu Ala
            180                 185                 190

His Ala Phe Ala Pro Gly Thr Gly Val Gly Gly Asp Ser His Phe Asp
        195                 200                 205

Asp Asp Glu Leu Trp Thr Leu Gly Glu Gly Gln Val Val Arg Val Lys
    210                 215                 220

Tyr Gly Asn Ala Asp Gly Glu Tyr Cys Lys Phe Pro Phe Leu Phe Asn
225                 230                 235                 240

Gly Lys Glu Tyr Asn Ser Cys Thr Asp Thr Gly Arg Ser Asp Gly Phe
                245                 250                 255

Leu Trp Cys Ser Thr Thr Tyr Asn Phe Glu Lys Asp Gly Lys Tyr Gly
            260                 265                 270

Phe Cys Pro His Glu Ala Leu Phe Thr Met Gly Gly Asn Ala Glu Gly
        275                 280                 285

Gln Pro Cys Lys Phe Pro Phe Arg Phe Gln Gly Thr Ser Tyr Asp Ser
    290                 295                 300

Cys Thr Thr Glu Gly Arg Thr Asp Gly Tyr Arg Trp Cys Gly Thr Thr
305                 310                 315                 320

Glu Asp Tyr Asp Arg Asp Lys Lys Tyr Gly Phe Cys Pro Glu Thr Ala
                325                 330                 335

Met Ser Thr Val Gly Gly Asn Ser Glu Gly Ala Pro Cys Val Phe Pro
            340                 345                 350

Phe Thr Phe Leu Gly Asn Lys Tyr Glu Ser Cys Thr Ser Ala Gly Arg
        355                 360                 365
```

```
Ser Asp Gly Lys Met Trp Cys Ala Thr Thr Ala Asn Tyr Asp Asp Asp
    370                 375                 380

Arg Lys Trp Gly Phe Cys Pro Asp Gln Gly Tyr Ser Leu Phe Leu Val
385                 390                 395                 400

Ala Ala His Glu Phe Gly His Ala Met Gly Leu Glu His Ser Gln Asp
            405                 410                 415

Pro Gly Ala Leu Met Ala Pro Ile Tyr Thr Tyr Lys Asn Phe Arg
        420                 425                 430

Leu Ser Gln Asp Asp Ile Lys Gly Ile Gln Leu Tyr Gly Ala Ser
            435                 440                 445

Pro Asp Ile Asp Leu Gly Thr Gly Pro Thr Pro Thr Leu Gly Pro Val
450                 455                 460

Thr Pro Glu Ile Cys Lys Gln Asp Ile Val Phe Asp Gly Ile Ala Gln
465                 470                 475                 480

Ile Arg Gly Glu Ile Phe Phe Phe Lys Asp Arg Phe Ile Trp Arg Thr
                485                 490                 495

Val Thr Pro Arg Asp Lys Pro Met Gly Pro Leu Leu Val Ala Thr Phe
                500                 505                 510

Trp Pro Glu Leu Pro Glu Lys Ile Asp Ala Val Tyr Glu Ala Pro Gln
        515                 520                 525

Glu Glu Lys Ala Val Phe Phe Ala Gly Asn Glu Tyr Trp Ile Tyr Ser
530                 535                 540

Ala Ser Thr Leu Glu Arg Gly Tyr Pro Lys Pro Leu Thr Ser Leu Gly
545                 550                 555                 560

Leu Pro Pro Asp Val Gln Arg Val Asp Ala Ala Phe Asn Trp Ser Lys
                565                 570                 575

Asn Lys Lys Thr Tyr Ile Phe Ala Gly Asp Lys Phe Trp Arg Tyr Asn
                580                 585                 590

Glu Val Lys Lys Lys Met Asp Pro Gly Phe Pro Lys Leu Ile Ala Asp
            595                 600                 605

Ala Trp Asn Ala Ile Pro Asp Asn Leu Asp Ala Val Val Asp Leu Gln
        610                 615                 620

Gly Gly Gly His Ser Tyr Phe Phe Lys Gly Ala Tyr Tyr Leu Lys Leu
625                 630                 635                 640

Glu Asn Gln Ser Leu Lys Ser Val Lys Phe Gly Ser Ile Lys Ser Asp
                645                 650                 655

Trp Leu Gly Cys
            660

<210> SEQ ID NO 2
<211> LENGTH: 20
<212> TYPE: PRT
<213> ORGANISM: Homo sapiens

<400> SEQUENCE: 2

Met Glu Ala Leu Met Ala Arg Gly Ala Leu Thr Gly Pro Leu Arg Ala
1               5                   10                  15

Leu Cys Leu Leu
            20

<210> SEQ ID NO 3
<211> LENGTH: 20
<212> TYPE: PRT
<213> ORGANISM: Homo sapiens

<400> SEQUENCE: 3
```

```
Thr Gly Pro Leu Arg Ala Leu Cys Leu Leu Gly Cys Leu Leu Ser His
 1               5                  10                  15
Ala Ala Ala Ala
            20

<210> SEQ ID NO 4
<211> LENGTH: 20
<212> TYPE: PRT
<213> ORGANISM: Homo sapiens

<400> SEQUENCE: 4

Gly Cys Leu Leu Ser His Ala Ala Ala Ala Pro Ser Pro Ile Ile Lys
 1               5                  10                  15
Phe Pro Gly Asp
            20

<210> SEQ ID NO 5
<211> LENGTH: 20
<212> TYPE: PRT
<213> ORGANISM: Homo sapiens

<400> SEQUENCE: 5

Val Ala Pro Lys Thr Asp Lys Glu Leu Ala Val Gln Tyr Leu Asn Thr
 1               5                  10                  15
Phe Tyr Gly Cys
            20

<210> SEQ ID NO 6
<211> LENGTH: 20
<212> TYPE: PRT
<213> ORGANISM: Homo sapiens

<400> SEQUENCE: 6

Arg Ile His Asp Gly Glu Ala Asp Ile Met Ile Asn Phe Gly Arg Trp
 1               5                  10                  15
Glu His Gly Asp
            20

<210> SEQ ID NO 7
<211> LENGTH: 20
<212> TYPE: PRT
<213> ORGANISM: Homo sapiens

<400> SEQUENCE: 7

Glu Ser Cys Thr Ser Ala Gly Arg Ser Asp Gly Lys Met Trp Cys Ala
 1               5                  10                  15
Thr Thr Ala Asn
            20

<210> SEQ ID NO 8
<211> LENGTH: 20
<212> TYPE: PRT
<213> ORGANISM: Homo sapiens

<400> SEQUENCE: 8

Gly Tyr Pro Lys Pro Leu Thr Ser Leu Gly Leu Pro Pro Asp Val Gln
 1               5                  10                  15
Arg Val Asp Ala
            20

<210> SEQ ID NO 9
<211> LENGTH: 20
```

```
<212> TYPE: PRT
<213> ORGANISM: Homo sapiens

<400> SEQUENCE: 9

Ala Phe Asn Trp Ser Lys Asn Lys Lys Thr Tyr Ile Phe Ala Gly Asp
1               5                   10                  15

Lys Phe Trp Arg
            20

<210> SEQ ID NO 10
<211> LENGTH: 20
<212> TYPE: PRT
<213> ORGANISM: Homo sapiens

<400> SEQUENCE: 10

Gly Phe Pro Lys Leu Ile Ala Asp Ala Trp Asn Ala Ile Pro Asp Asn
1               5                   10                  15

Leu Asp Ala Val
            20

<210> SEQ ID NO 11
<211> LENGTH: 20
<212> TYPE: PRT
<213> ORGANISM: Homo sapiens

<400> SEQUENCE: 11

Val Asp Leu Gln Gly Gly Gly His Ser Tyr Phe Phe Lys Gly Ala Tyr
1               5                   10                  15

Tyr Leu Lys Leu
            20

<210> SEQ ID NO 12
<211> LENGTH: 20
<212> TYPE: PRT
<213> ORGANISM: Homo sapiens

<400> SEQUENCE: 12

Phe Phe Lys Gly Ala Tyr Tyr Leu Lys Leu Glu Asn Gln Ser Leu Lys
1               5                   10                  15

Ser Val Lys Phe
            20

<210> SEQ ID NO 13
<211> LENGTH: 1983
<212> TYPE: DNA
<213> ORGANISM: Homo sapiens

<400> SEQUENCE: 13
atggaggcgc taatggcccg gggcgcgctc acgggtcccc tgagggcgct ctgtctcctg      60
ggctgcctgc tgagccacgc cgccgccgcg ccgtcgccca tcatcaagtt ccccggcgat     120
gtcgccccca aaacggacaa agagttggca gtgcaatacc tgaacacctt ctatggctgc    180
cccaaggaga gctgcaacct gtttgtgctg aaggacacac taagaagat gcagaagttc     240 tttggactgc cccagacagg tgatcttgac cagaatacca tcgagaccat gcggaagcca    300
cgctgcggca acccagatgt ggccaactac aacttcttcc ctcgcaagcc caagtgggac    360
aagaaccaga tcacatacag gatcattggc tacacacctg atctggaccc agagacagtg    420
gatgatgcct ttgctcgtgc cttccaagtc tggagcgatg tgaccccact gcggttttct    480
cgaatccatg atggagaggc agacatcatg atcaactttg ccgctgggga gcatggcgat    540
```

```
ggatacccct tgacggtaa ggacggactc ctggctcatg ccttcgcccc aggcactggt    600
gttgggggag actcccattt tgatgacgat gagctatgga ccttgggaga aggccaagtg    660
gtccgtgtga agtatggcaa cgccgatggg gagtactgca agttcccctt cttgttcaat    720
ggcaaggagt acaacagctg cactgatact ggccgcagcg atggcttcct ctggtgctcc    780
accacctaca actttgagaa ggatggcaag tacggcttct gtccccatga agccctgttc    840
accatgggcg gcaacgctga aggacagccc tgcaagtttc cattccgctt ccagggcaca    900
tcctatgaca gctgcaccac tgagggccgc acggatggct accgctggtg cggcaccact    960
gaggactacg accgcgacaa gaagtatggc ttctgccctg agaccgccat gtccactgtt   1020
ggtgggaact cagaaggtgc ccctgtgtc ttccccttca ctttcctggg caacaaatat   1080
gagagctgca ccagcgccgg ccgcagtgac ggaaagatgt ggtgtgcgac acagccaac   1140 tacgatgacg accgcaagtg gggcttctgc cctgaccaag ggtacagcct gttcctcgtg   1200
gcagcccacg agtttggcca cgccatgggg ctggagcact cccaagaccc tgggccctg   1260 atggcaccca tttacaccta caccaagaac ttccgtctgt cccaggatga catcaagggc   1320
attcaggagc tctatgggc ctctcctgac attgaccttg gcaccggccc cacccccaca   1380
ctgggccctg tcactcctga gatctgcaaa caggacattg tatttgatgg catcgctcag   1440
atccgtggtg agatcttctt cttcaaggac cggttcattt ggcggactgt gacgccacgt   1500
gacaagccca tggggcccct gctggtggcc acattctggc ctgagctccc ggaaaagatt   1560
gatgcggtat acgaggcccc acaggaggag aaggctgtgt ctttgcagg gaatgaatac   1620 tggatctact cagccagcac cctggagcga gggtaccca agccactgac cagcctggga   1680
ctgccccctg atgtccagcg agtggatgcc gcctttaact ggagcaaaaa caagaagaca   1740
tacatctttg ctggagacaa attctggaga tacaatgagg tgaagaagaa aatggatcct   1800
ggctttccca agctcatcgc agatgcctgg aatgccatcc ccgataacct ggatgccgtc   1860
gtggacctgc agggcggcgg tcacagctac ttcttcaagg gtgcctatta cctgaagctg   1920
gagaaccaaa gtctgaagag cgtgaagttt ggaagcatca aatccgactg ctaggctgc   1980 tga                                                                1983
```

```
<210> SEQ ID NO 14
<211> LENGTH: 60
<212> TYPE: DNA
<213> ORGANISM: Homo sapiens

<400> SEQUENCE: 14
atggaggcgc taatggcccg gggcgcgctc acgggtcccc tgagggcgct ctgtctcctg    60

<210> SEQ ID NO 15
<211> LENGTH: 60
<212> TYPE: DNA
<213> ORGANISM: Homo sapiens

<400> SEQUENCE: 15
acgggtcccc tgagggcgct ctgtctcctg ggctgcctgc tgagccacgc cgccgccgcg    60

<210> SEQ ID NO 16
<211> LENGTH: 60
<212> TYPE: DNA
<213> ORGANISM: Homo sapiens

<400> SEQUENCE: 16
ggctgcctgc tgagccacgc cgccgccgcg ccgtcgccca tcatcaagtt ccccggcgat    60
```

<210> SEQ ID NO 17
<211> LENGTH: 60
<212> TYPE: DNA
<213> ORGANISM: Homo sapiens

<400> SEQUENCE: 17
gtcgccccca aaacggacaa agagttggca gtgcaatacc tgaacacctt ctatggctgc      60

<210> SEQ ID NO 18
<211> LENGTH: 60
<212> TYPE: DNA
<213> ORGANISM: Homo sapiens

<400> SEQUENCE: 18
cgaatccatg atggagaggc agacatcatg atcaactttg ccgctggga gcatggcgat      60

<210> SEQ ID NO 19
<211> LENGTH: 60
<212> TYPE: DNA
<213> ORGANISM: Homo sapiens

<400> SEQUENCE: 19
gagagctgca ccagcgccgg ccgcagtgac ggaaagatgt ggtgtgcgac cacagccaac      60

<210> SEQ ID NO 20
<211> LENGTH: 60
<212> TYPE: DNA
<213> ORGANISM: Homo sapiens

<400> SEQUENCE: 20
gggtacccca agccactgac cagcctggga ctgcccctg atgtccagcg agtggatgcc       60

<210> SEQ ID NO 21
<211> LENGTH: 60
<212> TYPE: DNA
<213> ORGANISM: Homo sapiens

<400> SEQUENCE: 21
gcctttaact ggagcaaaaa caagaagaca tacatctttg ctggagacaa attctggaga      60

<210> SEQ ID NO 22
<211> LENGTH: 60
<212> TYPE: DNA
<213> ORGANISM: Homo sapiens

<400> SEQUENCE: 22
ggctttccca agctcatcgc agatgcctgg aatgccatcc ccgataacct ggatgccgtc      60

<210> SEQ ID NO 23
<211> LENGTH: 60
<212> TYPE: DNA
<213> ORGANISM: Homo sapiens

<400> SEQUENCE: 23
gtggacctgc agggcggcgg tcacagctac ttcttcaagg gtgcctatta cctgaagctg      60

<210> SEQ ID NO 24
<211> LENGTH: 60
<212> TYPE: DNA
<213> ORGANISM: Homo sapiens

<400> SEQUENCE: 24

```
ttcttcaagg gtgcctatta cctgaagctg gagaaccaaa gtctgaagag cgtgaagttt    60
```

<210> SEQ ID NO 25
<211> LENGTH: 9
<212> TYPE: PRT
<213> ORGANISM: Human immunodeficiency virus

<400> SEQUENCE: 25

Arg Lys Lys Arg Arg Gln Arg Arg Arg
 1               5